(12) United States Patent
Rodriguez et al.

(10) Patent No.: US 10,647,037 B2
(45) Date of Patent: May 12, 2020

(54) MECHANICAL RETICULATION OF POLYMERIC-BASED CLOSED CELL FOAMS

(71) Applicants: LAWRENCE LIVERMORE NATIONAL SECURITY, LLC, Livermore, CA (US); The Texas A&M University System, College Station, TX (US)

(72) Inventors: Jennifer N. Rodriguez, Lathrop, CA (US); Duncan J. Maitland, College Station, TX (US); Thomas S. Wilson, San Leandro, CA (US)

(73) Assignees: Lawrence Livermore National Security, LLC, Livermore, CA (US); The Texas A&M University System, College Station, TX (US)

( * ) Notice: Subject to any disclaimer, the term of this patent is extended or adjusted under 35 U.S.C. 154(b) by 380 days.

(21) Appl. No.: 15/232,619

(22) Filed: Aug. 9, 2016

(65) Prior Publication Data

US 2017/0043512 A1 Feb. 16, 2017

Related U.S. Application Data

(60) Provisional application No. 62/203,297, filed on Aug. 10, 2015.

(51) Int. Cl.
*B29C 44/56* (2006.01)
*C08J 9/38* (2006.01)
(Continued)

(52) U.S. Cl.
CPC .......... *B29C 44/5663* (2013.01); *A61L 31/06* (2013.01); *A61L 31/146* (2013.01); *B32B 5/18* (2013.01); *B32B 5/32* (2013.01); *C08G 18/3228* (2013.01); *C08G 18/3278* (2013.01); *C08G 18/3284* (2013.01); *C08G 18/73* (2013.01); *C08J 9/38* (2013.01); *A61L 2400/16* (2013.01); *B29K 2075/00* (2013.01); *B29K 2105/046* (2013.01); *B29K 2995/0093* (2013.01); *B32B 2266/0278* (2013.01); *B32B 2266/08* (2013.01);
(Continued)

(58) Field of Classification Search
None
See application file for complete search history.

(56) References Cited

U.S. PATENT DOCUMENTS

| 3,171,820 A | 3/1965 | Volz |
| 2005/0043585 A1 | 2/2005 | Datta et al. |

(Continued)

OTHER PUBLICATIONS

Singhal et al., "Controlling the Actuation Rate of Low-Density Shape-Memory Polymer Foams in Water", Macromol. Chem. Phys. 2013, 214, 1204-1214. (Year: 2013).*
(Continued)

*Primary Examiner* — Scott R. Walshon
*Assistant Examiner* — Elaine M Vazquez
(74) *Attorney, Agent, or Firm* — Trop, Pruner & Hu, P.C.

(57) ABSTRACT

Polymeric based closed cell foams, such as shape memory polymer foams, contain bubbles. Making these bubbles continuous is called reticulation. Disclosed are embodiments of a device and method to controllably reticulate polymer-based closed cell foams by puncturing the membranes of these polymer-based closed cell foams.

21 Claims, 8 Drawing Sheets

(51) Int. Cl.
  *A61L 31/06* (2006.01)
  *A61L 31/14* (2006.01)
  *C08G 18/73* (2006.01)
  *B32B 5/18* (2006.01)
  *B32B 5/32* (2006.01)
  *C08G 18/32* (2006.01)
  *B29K 105/04* (2006.01)
  *B29K 75/00* (2006.01)
  *C08G 101/00* (2006.01)

(52) U.S. Cl.
  CPC ...... *B32B 2535/00* (2013.01); *C08G 2101/00* (2013.01); *C08J 2205/052* (2013.01); *C08J 2207/10* (2013.01); *C08J 2375/04* (2013.01)

(56) References Cited

U.S. PATENT DOCUMENTS

| | | | |
|---|---|---|---|
| 2007/0135907 A1 | 6/2007 | Wilson et al. | |
| 2013/0089576 A1 | 4/2013 | Maitland | |
| 2014/0142207 A1* | 5/2014 | Singhal | A61B 17/0057 521/76 |
| 2014/0296358 A1 | 10/2014 | Maitland et al. | |

OTHER PUBLICATIONS

Van Der Burg et al., "On the Linear Elastic Properties of Regular and Random Open-Cell Foam Models," Journal of Cellular Plastics, vol. 33, 1997, pp. 31-54.

Metcalfe, et al., "Cold Hibernated Elastic Memory Foams for Endovascular Interventions," Biomaterials, 2003, vol. 24, pp. 491-497.

Rodriguez, J. N., et al., "Reticulation of low density shape memory polymer foam with an in vivo demonstration of vascular occlusion," Research Paper, Journal of the Mechanical Behavior of Biomedical Materials, 2014, 13 pages.

De Schampheleire, Sven, et al., "A Discussion on the Interpretation of the Darcy Equation in Case of Open-Cell Metal Foam Based on Numerical Simulations," Article, MDPI, Materials 2016, 15 pages.

Carley. James F., "Whittington's Dictionary of Plastics," Technomic Publishing Company, Inc., 1993, 4 pages.

FXI Innovations "Reticulated Polyurethane Foam," Process Foam Reticulation, http://fxi.com/foam-technologies/processes/reticulation.php 2016, 3 pages.

Andrew C. Weems, "Shape Memory Polyurethanes With Oxidation-induced Degradation: In Vivo and In Vitro Correlations for Endovascular Material Applications," Jun. 21, 2017, 12 pages.

* cited by examiner

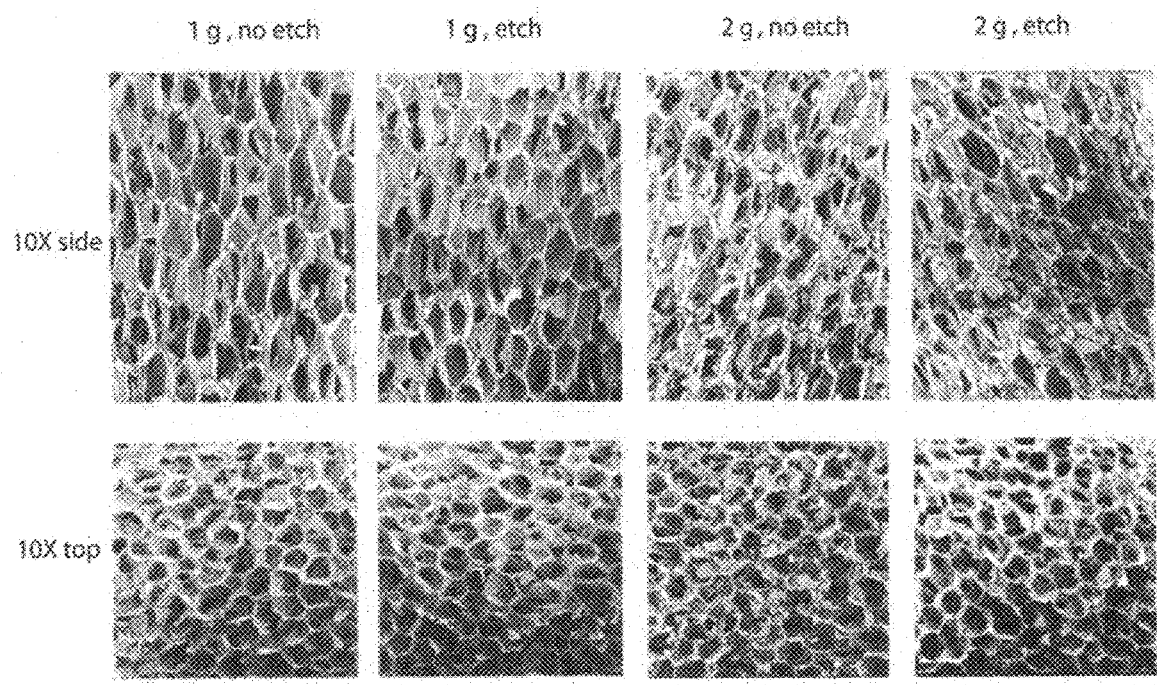
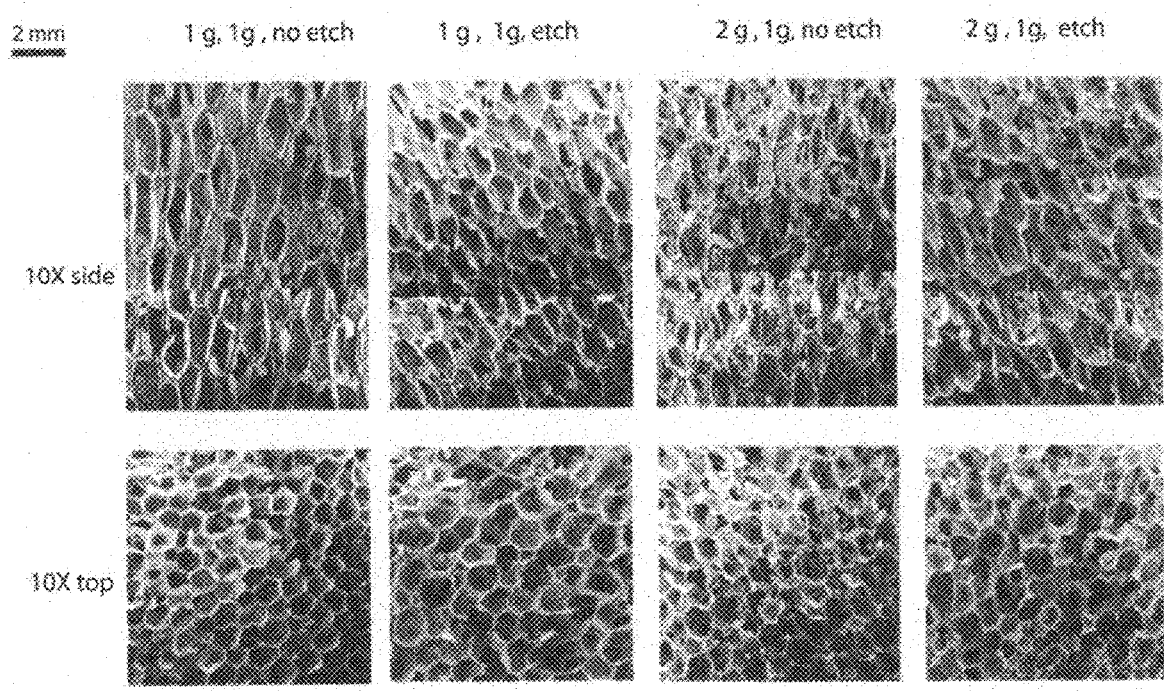
FIGURE 5

609  610

MECHANICAL RETICULATION OF POLYMERIC-BASED CLOSED CELL FOAMS

PRIORITY CLAIM

This application claims priority to U.S. Provisional Patent Application No. 62/203,297 filed on Aug. 10, 2015 and entitled "Mechanical Reticulation of Polymeric-Based Closed Cell Foams", the content of which is hereby incorporated by reference.

STATEMENT OF FEDERALLY FUNDED RESEARCH

This disclosure was made with government support under R01EB000462 awarded by the National Institutes of Health (NIH), National Institute of Biomedical Imaging and Bioengineering. The government has certain rights in the invention. Furthermore, the United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

Polymeric-based closed cell foams contain air bubbles that are isolated from one another. Reticulation is the process by which these bubbles are made continuous through removal of some of the membranes of the polymeric-based closed cell foams. Chemical or thermal methods are used to reticulate polymeric-based closed cell foams. Chemical etching involves running the polymeric-based closed cell foams through a caustic bath. The caustic bath chemically dissolves the membrane between the pores, leaving only struts of the polymeric-based closed cell foam. Thermal reticulation involves the use of an explosive gas within a vacuum pressure vessel to burn the membranes of the polymeric-based closed cell foam, leaving the struts of the polymeric-based closed cell foam intact.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIG. 4(A) shows horizontal (x-y) planes and FIG. 4(B) vertical (x-z) planes. The cells are elongated in the direction of the foam rise (z, vertical). The membranes between cells are evident.

FIG. 5 includes Scanning Electron Microscopy (10X magnification, scale bar=2 mm) of reticulated foam samples of embodiments. The cases are summarized in Table 1.

DETAILED DESCRIPTION

Figure 1:
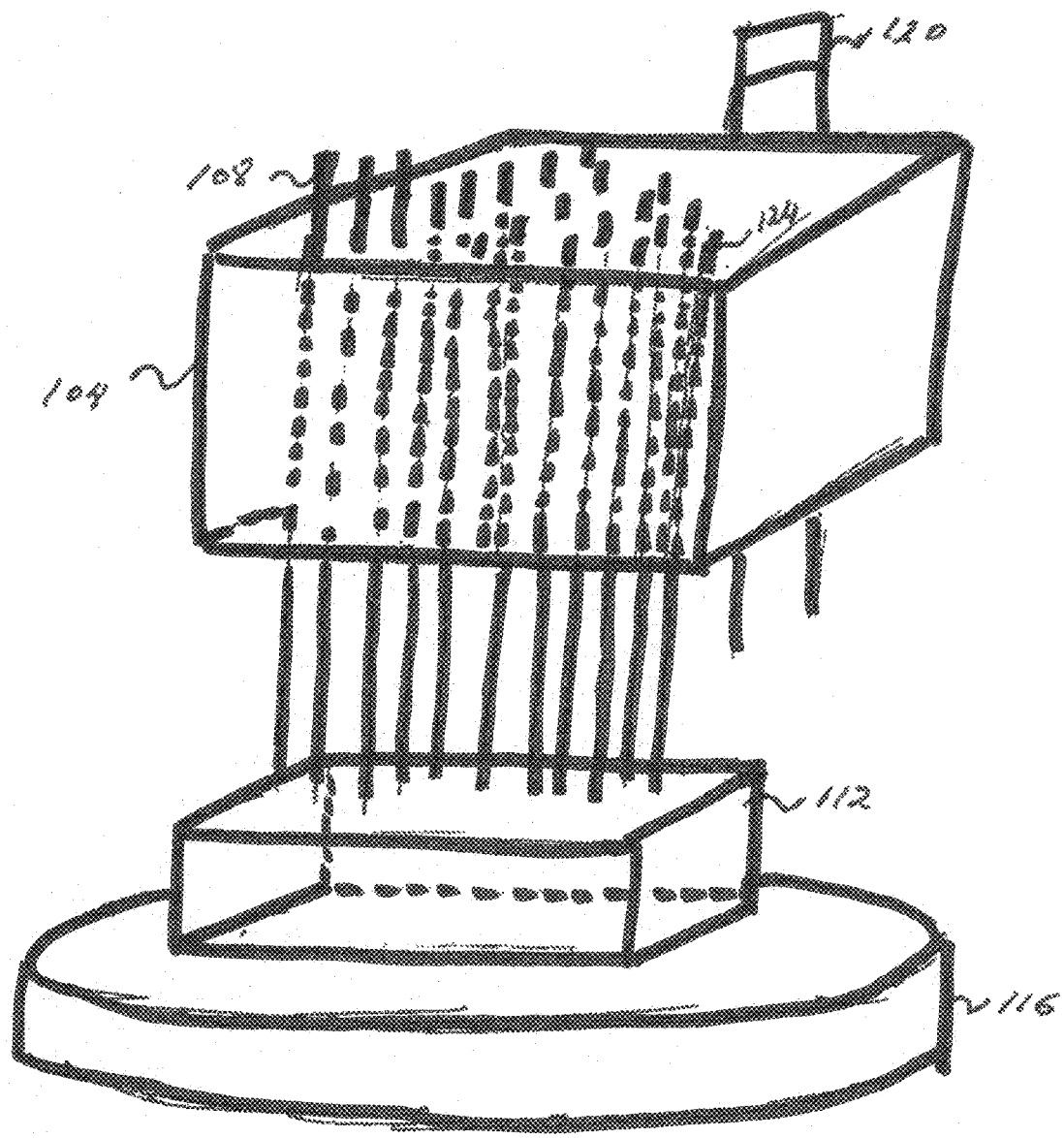
FIG. 1 depicts an example device to reticulate polymeric-based closed cell foams according to an embodiment.

Reference will now be made to the drawings wherein like structures may be provided with like suffix reference designations. In order to show the structures of various embodiments more clearly, the drawings included herein are diagrammatic representations of structures. Thus, the actual appearance of the structures, for example in a photomicrograph, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact.

The aforementioned chemical and thermal etching methods to reticulate polymeric-based closed cell foams are efficient. However, Applicant determined neither method is effective in controlling the amount of reticulation. For example, Applicant determined being able to control the amount of reticulation so that a polymeric-based closed cell foam can be used for biomedical applications would be useful. Applicant further determined a system and method capable of tuning the amount of reticulation of polymeric-based closed cell foams would be desirable.

Various embodiments are disclosed for the controlled, mechanical reticulation of polymeric-based closed cell foams. In one aspect of the disclosure, a device is disclosed for the controlled reticulation of polymeric-based closed cell foams. Controlled reticulation means that the quantity of membranes of the sample of the polymeric-based closed cell foam that are reticulated can be regulated. For example, the total number of reticulated membranes may be controlled. Further, the total amount of an individual membrane that is reticulated may be controlled (e.g., a single membrane may be punctured and occupy 25, 45, 65% of the original 100% coverage between struts of a cell).

The device includes an array in an embodiment. The array includes a plurality of channels, each channel capable of receiving a needle. Thus, the array can contain a plurality of needles. The device can include a shaker, capable of receiving a sample of a polymeric-based closed cell foam. The shaker can oscillate in at least one axis (e.g. any of the x, y, or z directions). The oscillation of the shaker can cause a downward motion of the plurality of needles of the array into the sample of the polymeric-based closed cell foam. This downward motion of the plurality of needles of the array may be due, at least in part, to gravity. As the plurality of needles of the array penetrate into the sample of the polymeric-based closed cell foam, the plurality of needles of the array controllably puncture the membranes of the polymeric-based closed cell foam, thereby controllably reticulating the polymeric-based closed cell foam.

In another aspect of the disclosure, the array can be chucked into or suspended from a milling machine or other device capable of controlled, stepwise motion. Through this controlled, stepwise motion, a sample of polymeric-based closed cell foam on the shaker can be reticulated. In some embodiments of the device, the sample of polymeric-based closed cell foam can be reticulated in three axes (e.g. x, y, and z directions).

Another aspect of the disclosure includes a method to controllably reticulate polymeric-based closed cell foams. In an embodiment, the reticulation can be accomplished through removing membranes of the polymeric-based closed cell foam through mechanical agitation of the polymeric-based closed cell foam in at least one axis. Such mechanical agitation can include piercing the membranes of the polymeric-based closed cell foam.

In an embodiment, the disclosed device can be used to reticulate polymeric-based closed cell foams. The shaker of the disclosed device can receive a sample of the polymeric-based closed cell foam. The polymeric-based closed cell foam can be mechanically agitated by causing the shaker of the disclosed device to oscillate vertically. This vertical oscillation can induce the plurality of needles of the array of the disclosed device to move towards the sample of the polymeric-based closed cell foam, such motion due, at least in part, to gravity (however in other embodiments the motion may be motor driven). As the needles penetrate the sample of the polymeric-based closed cell foam, the needles break membranes of the sample of the polymeric-based closed cell foam, thereby reticulating the sample.

The description provided herein includes exemplary devices, methods and techniques that embody aspects of the disclosure. However, it is understood that the described embodiments might be practiced without these specific details. For instance, although examples refer to a plurality of needles employed to compromise the membranes of polymeric-based closed cell foams, any device that is capable of piercing the membranes of polymeric-based closed cell foams in a controlled manner can be employed in some embodiments. Moreover, while examples refer to agitation of a sample of a polymeric-based closed cell foam to compromise the membranes of these polymeric-based closed cell foams, any technique through which the membranes of such polymeric-based closed cell foams might be compromised in a controlled fashion can be employed to reticulate the polymeric-based closed cell foams in an embodiment.

Controlled removal of the membranes of a polymeric-based closed cell foam can be useful for a variety of purposes including biomedical applications. Controlling the quantity of the membranes of a sample of polymeric-based closed cell foam that are removed is advantageous, because, in some applications of the polymeric-based closed cell foams, more membranes should be removed, while in other applications of the polymeric-based closed cell foams, fewer membranes should be removed. Embodiments of the disclosed device and method can be employed to control the quantity of membranes in a sample of polymeric-based closed cell foam that are pierced, leaving the base structure of the struts of the polymeric-based closed cell foam intact. The disclosed device and method can be employed to pierce the membranes of a sample of polymeric-based closed cell foam in one, two, or three dimensions.

FIG. 1 is an example of an embodiment of the disclosed device. In one embodiment, the device may include an array 104. The array 104 can be permeated with perpendicular, low-friction channels 124. Each channel 124 can be capable of receiving a needle or pin 108. Each channel 124 can be capable of permitting the vertical motion of the needle 108 placed within the channel 124 due to the low friction surface of the channel 124. In an embodiment, the array 104 can be comprised of a delrin block with channels 124 drilled into the delrin block. In an embodiment, each needle 108 may be comprised of a nitinol alloy. For example, in an embodiment, each needle 108 can be fabricated by casting a nitinol wire in a 1 ml syringe filled with EpoxAcast® 690 doped with less than 1 μm tungsten particulate (see FIG. 3(c)). However, the needles 108 can be fabricated from other alloys capable of piercing the membranes of polymeric-based closed cell foams. The device can include a shaker 116. A sample of a polymeric-based closed cell foam 112 can be mounted on the shaker 116. The shaker 116 can be any device capable of producing vertical oscillations (or other oscillations in other embodiments such as horizontal oscillations). For instance, the shaker 116 can be an Analysette 3 Spartan Pulverisette in one embodiment. The device can include a holder 120 to suspend the array 104 above the sample of the polymeric-based close cell foam 112. In an embodiment, the holder 120 can be a milling machine, and the array 104 can be chucked in the milling machine. In other embodiments, the holder 120 can be any device that can be used to suspend or chuck the array 104. The holder 120 can be a device capable of moving the array 104 in a horizontal step-wise fashion (i.e., from left to right along the top plane of foam 112).

Figure 2:
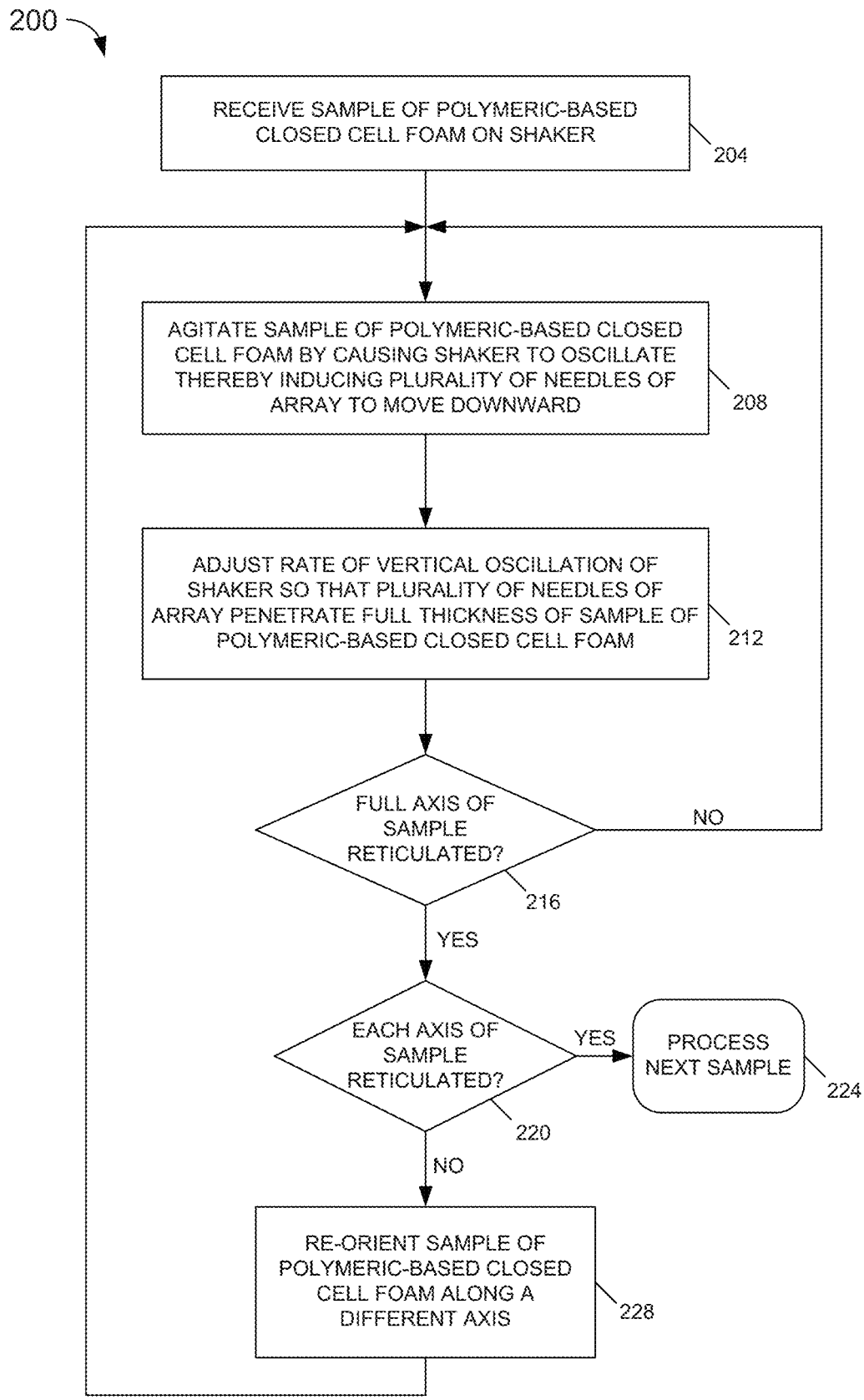
FIG. 2 is a flow diagram illustrating example operations by which a polymeric-based closed cell foam may be reticulated according to an embodiment.

FIG. 2 is a flow diagram 200 illustrating example operations by which a polymeric-based closed cell foam may be reticulated according to an embodiment of this disclosure. At 204, a sample of a polymeric-based closed cell foam is received on the shaker of a device like the one depicted in FIG. 1. At 208, the sample of polymeric-based closed cell foam is agitated by causing the shaker to oscillate, thereby inducing the plurality of needles, like the ones depicted in FIG. 1, of the array to move downward into the sample of the polymeric-based closed cell foam due, at least in part, to gravity. At 212, the rate of vertical oscillation of the shaker can be adjusted so that the plurality of needles of the array penetrates the full thickness of the sample of polymeric-based closed cell foam. At 216, it can be determined whether a full axis of the sample of polymeric-based closed cell foam has been reticulated. For instance, it can be determined whether the entire z axis of the sample of polymeric-based closed cell foam has been reticulated. In an embodiment, if the entire axis of the sample of polymeric-based closed cell foam has not been reticulated, then the flow can return to 208 and 212. Otherwise, the flow can proceed to 220. At 220, it can be determined whether each axis of the sample of the polymeric-based closed cell foam has been reticulated. In an embodiment, if each axis of the sample of the polymeric-based closed cell foam has not been reticulated, the flow can proceed to 228. At 228, the sample of polymeric-based closed cell foam can be re-oriented along a different axis (i.e., an axis that has not been reticulated), and the flow can proceed through 208 through 220. In an embodiment, if each axis of the sample of polymeric-based closed cell foam has been reticulated, the flow can proceed to 224. At 224, the shaker can receive another sample of polymeric-based closed cell foam to reticulate. The user may wish to reticulate only along 1 axis in some embodiments.

Regarding block 212, one or more aspects of agitation may be adjusted. For example, the amplitude and/or frequency of vertical oscillation may be changed. Doing so may avoid an oscillation that is too extreme (which could cause needles to move downward with too great force possibly destroying struts instead of gradually bouncing or shifting away from relatively stronger struts to relatively weaker struts) or too conservative (which could cause the needles lack the energy required to even penetrate relatively weak membranes and/or take too long to traverse an axis and reticulate a foam sample).

Figure 3:
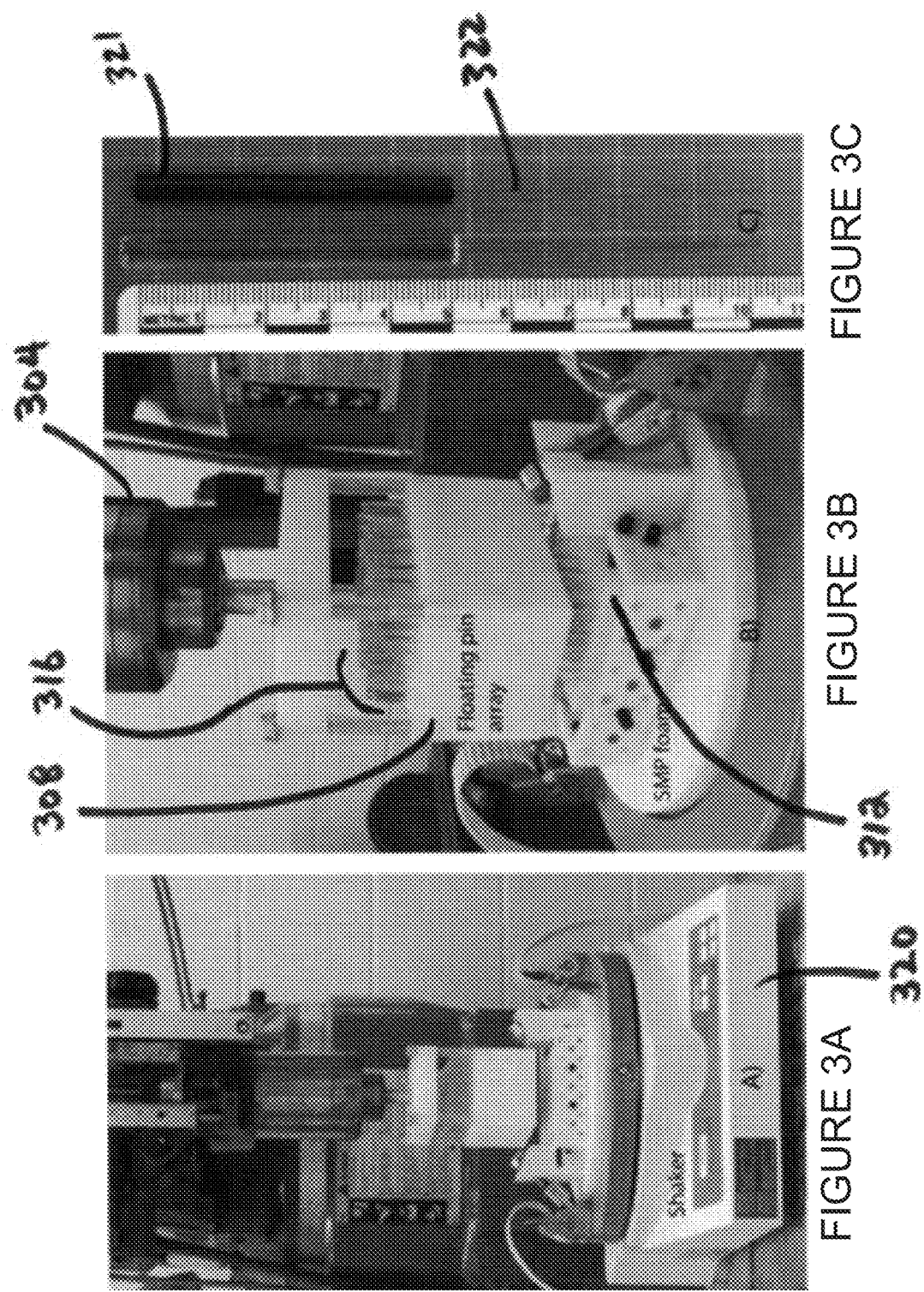
FIG. 3(A) shows an embodiment of a mechanical reticulation system including a floating nitinol pin array and vibratory foam shaker.
FIG. 3(B) shows a close up of an embodiment of the array punching the foam.
FIG. 3(C) shows an embodiment of nitinol pins cast in non-doped (left pin) and tungsten-doped polymer (right pin).

FIGS. 3(a), 3(b), 3(c) depict embodiments of the disclosed device. In an embodiment, the disclosed device includes an array 308. The array 308 includes a plurality of needles 316 (also referred to as pins). The array 308 can be fabricated from a delrin block, which has been drilled to include individual channels, each channel capable of accepting a needle 316. These low friction channels, drilled into the delrin block, permit a vertical motion of the needles 316. The array 308 can be fabricated from materials other than delrin. For instance, the array 308 can be fabricated from any materials that can be configured to include low-friction channels capable of accepting needles 316. The array 308 can be chucked into a milling machine 304, such as a Bridgeport milling machine as an example. An embodiment of the device can include a shaker 320. The shaker 320 can be configured to receive a sample of polymeric-based closed cell foam 312. Each needle 316 of the plurality of needles 316 can be fabricated by casting a nitinol wire in a 1 ml syringed filled with ExpoxAcast® 690 doped with less than 1 µm tungsten particulate in some embodiments. In other embodiments, each needle 316 can be fabricated from an alloy capable of piercing membranes of a polymeric-based closed cell foam.

In an embodiment, the plurality of needles 316 can be configured to contact a sample of polymeric-based closed cell foam 312. For instance, a sample of a polymeric-based closed cell foam 312 can be placed on a shaker 320. The shaker 320 can receive instructions to oscillate vertically, permitting a downward motion of the plurality of needles 316 into the sample of polymeric-based closed cell foam 312. The shaker 320 can be configured to continue to oscillate vertically so that the plurality of needles 316 penetrates a thickness of the sample of polymeric-based closed cell foam 312. In an embodiment, the array 308 can be chucked into a Bridgeport milling machine 304 for controlled step-wise movement, the milling machine 304 moving the array 308 horizontally. The sample of polymeric-based closed cell foam 312 can be reticulated (or punched) in a step-wise manner every 500 µm in one embodiment. In some embodiments, the sample of polymeric-based closed cell foam 312 can be reticulated along a single axis (x, y, or z) or multiple axes.

In an experimental embodiment of the disclosed device, needles of varying mass were made by varying the quantity of tungsten in the needle. Needles were made with masses of 0.25, 0.5, 0.75, 1.0, 1.5, 2.0, 2.5, and 3.0 g. These needles were used to axially reticulate through 30 mm of shape memory polymer (SMP) foam, a type of polymeric-based closed cell foam.

The average and median mechanical load that can puncture a single membrane using an experimental embodiment of the disclosed device were determined. The average and median mechanical load used to puncture a single membrane of a sample of a polymeric-based closed cell foam was determined to be 2.07±2.23 g and 1.27 g in the axial direction and 1.13±1.09 g and 0.80 g in the trans-axial direction respectively. The friction experienced by the plurality of needles of an experimental device was determined as the needles penetrated a sample of a polymeric-based closed cell foam. Friction during penetration of the plurality of needles through the polymeric-based closed cell foam was determined to be 0.12 g/mm.

In particular, Table 1 summarizes experiments performed using embodiments:

TABLE 1

Reticulation schemes employed for mechanical testing of foams.

|  | Nitinol needle mass | Chemical etch | Number of samples tested |
|---|---|---|---|
| Uni-axial | 1 g axial | No | 5 |
|  | 1 g axial | Yes | 5 |
|  | 2 g axial | No | 5 |
|  | 2 g axial | Yes | 5 |
| Tri-axial | 1 g axial, 1 g trans-axial | No | 5 |
|  | 1 g axial, 1 g trans-axial | Yes | 5 |
|  | 2 g axial, 1 g trans-axial | No | 5 |
|  | 2 g axial, 1 g trans-axial | Yes | 5 |
| Non-reticulated control | Not applicable | No | 5 |

Experimental samples were uni-axially reticulated (Z) and tri-axially reticulated (X, Y, Z), each experiment performed with a nitinol needle mass of 1 g and 2 g as shown in FIG. 6.

Elastic moduli for polymeric-based closed cell foams reticulated using embodiments were determined. Reticulation reduced the elastic modulus of each sample of the polymeric-based closed cell foam with the tri-axially reticulated samples of the polymeric-based closed cell foams having the lowest elastic moduli. The more extensive disruption of the cell membranes caused by reticulation in multiple axes resulted in a higher reduction of the elastic modulus.

The average stress versus strain curves for those samples, as listed in Table 1, of polymeric-based closed cell foams tested using an experimental embodiment of the disclosed device were determined. The non-reticulated foam had the highest stress plateau before densification, followed by the uni-axially and tri-axially reticulated polymeric-based closed cell foam samples.

Embodiments can be used to reticulate low-density SMP foams, a class of polymeric-based closed cell foams. For instance, an embodiment was used in the non-destructive reticulation of a SMP foam to disrupt the membranes between pore cells. In an embodiment, this reticulation resulted in a reduced elastic modulus and increased permeability of the SMP foam, while maintaining the shape memory behavior of the SMP foam. In embodiments, such reticulated foams were capable of achieving rapid vascular occlusion in an in vivo porcine model.

At least some of the contents provided herein are disclosed in Rodriguez, J.; Miller, M.; Boyle, A.; Horn, J.; Yang, C.; Wilson, T.; Ortega, J.; Small, W.; Nash, L.; Skoog, H.; and Maitland, D., Reticulation of low density SMP foam with an in vivo demonstration of vascular occlusion, Journal of the Mechanical Behavior of Biomedical Materials 40 (2014): 102-114.

An intracranial aneurysm, or abnormal bulging of an artery wall within the brain, is susceptible to rupture, having a great potential to result in mental debilitation or death. Rupture of an aneurysm, or subarachnoid hemorrhage, results in bleeding out into the spaces of the brain. The cause of aneurysm growth and rupture is not fully known, but is thought to be due to abnormal blood flow patterns, local shear stresses and the weakened state of the arterial wall. Due to the inability to predict the occurrence of a rupture of such a malformation, and its potential to have a fatal or harmful outcome, it is advantageous for the patient to be treated as early in the disease progression as possible.

In the past couple of decades, endovascular treatment has become the preferred treatment versus surgical methods. This is mainly due to the significantly less invasive nature of endovascular treatments, with attendant reductions in recovery time and cost when compared to surgical craniotomy. Previously, it has been shown that polyurethane based SMP foam is a biocompatible material effective for aneurysm filling in a porcine animal model. Additionally, other non-SMP polyurethane and polycarbonate foams have been explored for the purpose of vascular and abdominal aortic aneurysm occlusion with promising results. Embodiments provide a self-actuating vascular occlusion device (VOD) made of SMP foam to be delivered via endovascular methods.

Polyurethane based SMP formulations can be tailored to be blown into foams with various actuation temperatures, densities and pore cell sizes. These ultra-low density SMP materials have the ability to be temporarily programmed to a secondary compressed shape and maintain that shape until the material's temperature is elevated above its transition temperature. Around the transition temperature, the material regains its original shape. This ability to maintain a compressed shape until exposed to an increase in temperature above its transition temperature makes these materials excellent candidates for endovascular applications. Given their shape memory capability, tunable pore cell size, tunable actuation temperature and proven biocompatibility, embodiments include these materials as an endovascularly delivered VOD.

These foams possess a predominantly closed cell microstructure, which may not be optimal for aneurysm occlusion and subsequent healing. Post processing to reticulate the foam, or remove/puncture the thin membranes between pore cells while leaving the net-like foam backbone intact, enables blood flow to more easily permeate throughout the foam, and allow for a forming clot to stabilize the device within the aneurysm. This permeation of blood throughout the material also enables the desired cellular components necessary to induce healing to more easily migrate into the volume of foam after clotting has occurred.

As used herein, struts surround an intact membrane. Struts are thicker than membranes and are primarily responsible for structural integrity (e.g., Young's modulus) of the foams. A strut of a foam includes a bar, rod, or built-up member that resists pressure or thrust in the foam framework. A membrane, in contrast, includes a thin, pliable, sheet or layer, which forms a barrier or lining between two adjacent cells. With struts intact and a membrane between the struts that is also intact there will be barrier between adjoining cells but with struts intact but no complete membrane between the struts there will be no barrier between adjoining cells. In FIG. 4(b) a confluence of struts make vertices 401, 403 with strut 402 coupling vertices 401, 403 to each other. Membrane 404 is shown fully intact and separating one cell from another cell.

Reticulation has been achieved by multiple post-processing methods within industry, including caustic leaching via exposure of the foam to a caustic bath for a specific amount of time, temperature and speed, thermal reticulation via a controlled burning of the membranes with the ignition of hydrogen and oxygen gases within a vessel housing the foam, or cyclic loading and unloading of the material. The act of reticulation changes the overall physical properties of foam. With removal of membranes there is a decrease in the resistance to mechanical compression. There is also an increase in tensile properties, such as elongation and tearing strength. Embodiments provide a reticulation procedure for SMP foam whereby care is taken to avoid damaging the foam struts to preserve shape memory behavior and minimize the impact on its mechanical properties. For example, using gravity to force flexible needles through foams, coupled with oscillation, helps the needles bounce away from stronger struts and instead penetrate weaker membranes (thereby preserving struts and mechanical properties (e.g., Young's modulus) of foams).

An embodiment includes a methodology for reticulation of membranes between the pores of SMP foam without damaging the native structure or shape memory ability. The embodiment may be used as a VOD but may also be used in other areas such as insulation for buildings, cars, shock absorption, mechanical filtration, and the like. An embodiment includes a viable non-destructive method of reticulation involving mechanical membrane puncture (and in some embodiments, but not all embodiments, supplemental chemical etching). The effect of reticulation on the mechanical properties of the foam was determined. The occlusion time for VOD embodiments was determined via catheter implantation of reticulated foam devices within the vasculature of a porcine animal model. Such VODs are useful for aneurysm treatment or other vascular applications aimed at achieving hemostasis (e.g., wound dressings).

1. Materials and Methods 1.1. Foam Synthesis

Figure 4:
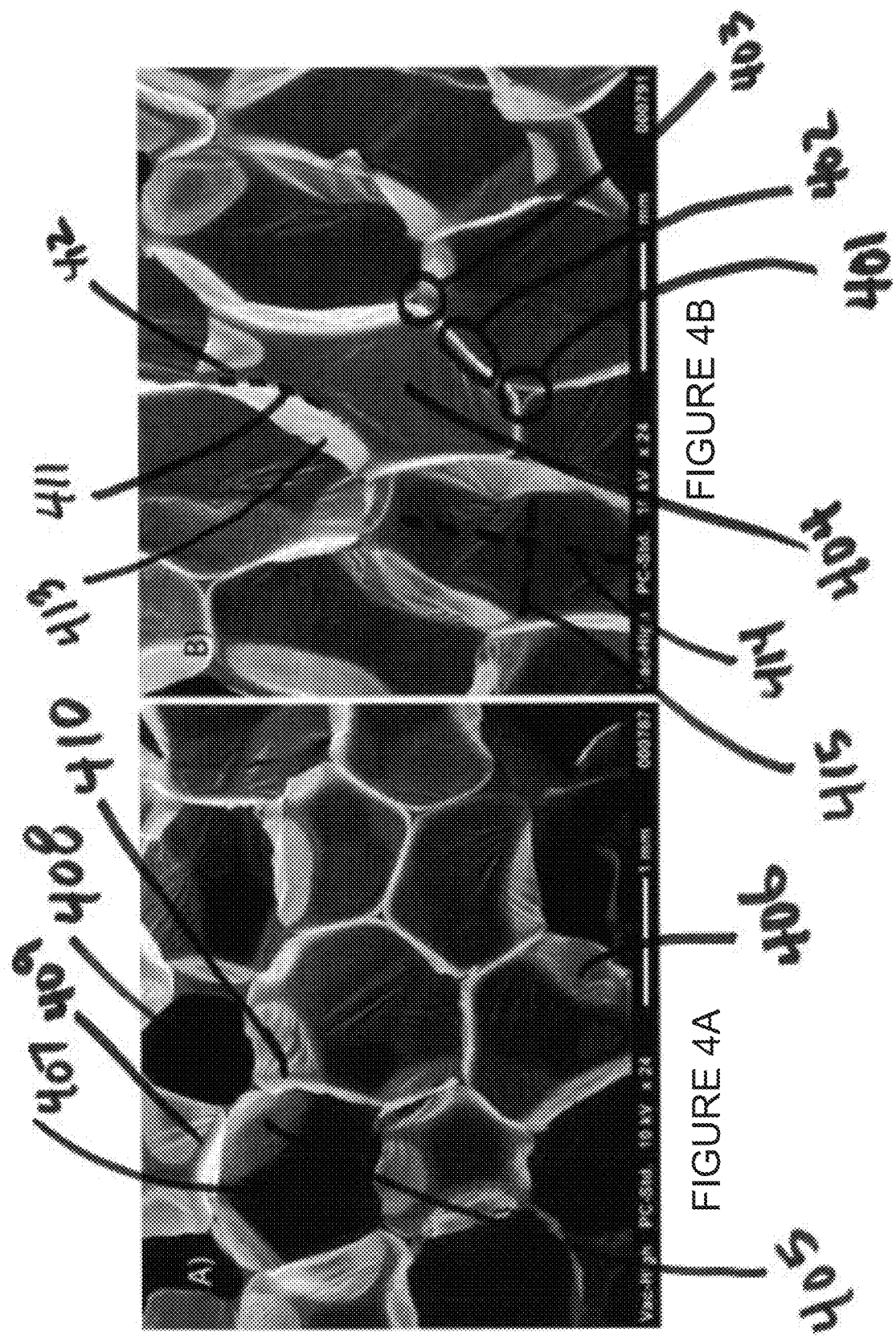
FIGS. 4(A) and 4(B) provide SEM cross-section images of embodiments of a native unreticulated SMP foam.

Two versions of SMP foam were fabricated by the method described by Singhal et al. (See Controlling the Actuation Rate of Low-Density Shape-Memory Polymer Foams in Water; Macromol. Chem. Phys. 2013, 214, 1204-1214). One version contained 100% hexamethylene diisocyanate (HDI) and the other contained 20% HDI and 80% trimethyl-1,6-hexamethylene diisocyanate (TMHDI) for the isocyanate monomer in the polyurethane reaction. The less hydrophobic 100% HDI foam was made specifically for vessel implantation studies (but is not so limited in other embodiments) to allow for immediate self-actuation of the VOD in vivo without the need for external heating. The foam actuates at body temperature after exposure to moisture in the blood which causes a drop in the material's transition temperature. Both foams were reticulated and chemically post-processed in the same manner. Aside from their different hydrophobicities, these two foams share very similar mechanical properties and shape memory characteristics. During the foaming process, the material is constrained by the side walls of the container and unconstrained from above as it rises. Due to these conditions and their ultra-low densities, the foams have an anisotropic morphology as demonstrated in FIGS. 4(A)-(B). FIG. 4 provides SEM cross-section images of native SMP foam in (A) horizontal (x-y) and (B) vertical (x-z) planes. The cells are elongated in the direction of the foam rise (z, vertical), as shown in FIG. 4(B). The membranes 404, 405, 406 between cells are evident. For example, membrane 405 separates cell 407 from cell 408. Cells 407, 408 have skeletal support including struts 409, 410.

1.2. Nitinol Wire Characterization

Nitinol wire pins were chosen as the means of mechanically reticulating the foam. Straight drawn nitinol wire (0.008" diameter) was purchased from Nitinol Devices & Components, Inc. (Fremont, Calif.), and was tested via strain to failure according to ASTM F2516-07 Standard Test Method for Tension Testing of Nickel-Titanium Superelastic Materials. Tests were performed on six samples using an Instron 5965 load frame (Instron©, Norwood, Mass.) equipped with a 500 N load cell. The Young's modulus and buckling load (critical load at which a column bows outward) of the nitinol wire were calculated. Young's modulus was calculated as the ratio of true stress to true strain at low strain. The buckling load was determined from the Euler column formula: $F_{cr}=\pi^2EI/(KL)^2$ where $F_{cr}$ is the minimal buckling load, K accounts for the end conditions, E is the Young's modulus, L is the length of the column and I is the area moment of inertia for the cross section of a cylindrical column, a circle, given by: $I=(\pi/4)R^4$ where R is the radius of the column. The end conditions, K, are determined as follows: both ends fixed: K=0.5, one end fixed, one end pivots: K=0.707, both ends pivot: K=1, one end fixed, one end free: K=2. Since the end of the nitinol pin is free to move laterally when interacting with the foam surfaces, K was taken to be 2.

1.3. Mechanical Reticulation System

The mechanical reticulation system consisted of two main components: (1) a gravity-driven floating nitinol pin array and (2) a vertically oscillating vibratory shaker upon which the foam was mounted for reticulation (FIGS. 3(A) and 3(B)). Each pin was made by casting a nitinol wire in a 1 ml syringe filled with EpoxAcast® 690 (Smooth-On, Inc., Easton, PA) doped with <1 μm tungsten particulate (Alfa Aesar, Ward Hill, MA). A 50-mm length of nitinol protruded from the cast polymer cylinder (FIG. 3(C)). The pins were loaded perpendicular to the top surface of the foam in individual channels drilled in a delrin block. The low-friction channels allowed unrestricted vertical motion of the pins (so that once the block was lowered to a level the pins contacted the foam, the pins were free to proceed through the foam based on gravity and oscillation without hindrance from the channels). The pins were spaced 7 mm apart in a radial pattern. With the free ends of the floating nitinol pins in contact with the foam, the foam was agitated (0.25 mm amplitude) by the vertically oscillating shaker (Fritsch, Analysette 3 Spartan pulverisette 0), allowing for gravity-driven downward movement of the pins. Agitation continued until the pins penetrated the full thickness of the foam. The delrin block, which was chucked into a Bridgeport milling machine (Hardinge Inc., Elmira, NY) for controlled step wise movement, was then translated horizontally (pins removed) for further reticulation of the foam sample. In an embodiment, the block has a shoulder that should the block be raised a certain amount the cast portion of the pin will catch the block and rise with the block, thereby allowing the pins to be stepped horizontally for reticulation in the same plane or for rotation of the block and/or pins to allow for reticulation in another plane. Samples were punched in a raster manner every 500 μm (i.e., via stepping across a single plane of the foam). The samples were punched in one axis (uni-axial) or three axes (tri-axial). Uni-axial reticulated samples were punched along the direction of foam rise only (z-axis). Tri-axial reticulated samples were punched along the x-, y-, and z-axes by punching along one axis, re-orienting the foam, and punching along a different axis.

FIG. 3(A) shows mechanical reticulation system including the floating nitinol pin array and vibratory foam shaker. FIG. 3(B) shows a close up of the array punching the foam. FIG. 3(C) shows nitinol pins cast in non-doped (left pin) and tungsten-doped polymer (right pin).

1.4. Preliminary Mechanical Reticulation Testing

To determine the pin mass necessary to puncture a 30-mm-thick foam sample using the mechanical reticulation system, pins of variable mass were made by varying the amount of tungsten in the cast pins (thus pin "mass" entails more than the mass of just the nitinol pin). Pins were made with masses of 0.25, 0.5, 0.75, 1.0, 1.5, 2.0, 2.5 and 3.0 grams. Uni-axial reticulation was performed to assess the effect of pin mass.

In addition to the method of varying the pin mass using the reticulation system, the membrane strength (minimal force necessary to puncture a membrane) and the friction of a wire passing through the foam were determined via mechanical testing using the Instron load frame equipped with a 50 N load cell. Agitation of the foam was not employed in these tests. A custom grip incorporating a pin vise was used to hold the 0.008" nitinol wire perpendicular to the foam sample. The wire extended 50 mm beyond the grip. All measurements were taken at ambient temperature. The force necessary to puncture a single membrane was determined in both the axial (foam rise) and trans-axial (orthogonal to foam rise) directions to assess potential differences due to the anisotropic foam cell structure. The force necessary to puncture a membrane was determined as the first spike in force prior to a sharp decrease in force encountered within the first 2 mm of foam. This distance was chosen due to the average pore cell size being roughly 1 mm in diameter. Force spikes greater than 10.5 g were likely caused by direct interaction with a strut, not a membrane, and were ignored. One hundred and fifty four (154) measurements in the axial direction and 153 measurements in the trans-axial direction were made. For measurement of friction between the nitinol wire and the foam as it penetrated through the 30-mm-thick foam, the crosshead was translated at a rate of 1 mm/min while the load was recorded. Two separate measurements were made. The friction was determined as the slope of the load vs. extension data, excluding the spikes where the nitinol wire tip directly contacted a membrane or strut.

1.5. Chemical Etching and Final Cleaning

In specified cases mechanical reticulation was supplemented by chemical etching (which is not required in all embodiments) to assess the effect of more thorough membrane removal as opposed to membrane puncture. To attempt to remove residual membranes after mechanical reticulation the foams were immersed into a 5N NaOH solution for 30 minutes while sonicated using a 5510R-DTH and 3510R-DTH ultrasonic cleaner (Branson® Ultrasonics Corp., Danbury, Conn.). The samples were then repeatedly rinsed with RO water to neutralize the samples. All samples (etched or not) were finally cleaned using the protocol outlined by Rodriguez et al. in 2013 (Rodriguez, J. N., Clubb, F. J., Wilson, T. S., Miller, M. W., Fossum, T., Hartman, J., Tuzun, E., Singhal, P., Maitland, D. J., 2013. In vivo response to an implanted shape memory polyurethane foam in a porcine aneurysm model. J. Biomed. Mater. Res. Part A 102 (5), 1231-1242). The samples were then dried for approximately three hours under vacuum at 90° C.

1.6. Imaging Foam Microstructure

Dried foam samples were sputter coated with gold using a Cressington 108 sputter coater, model 6002-8 (Ted Pella, Inc., Redding, Calif.) for 60 seconds at a distance of 3 cm. Imaging of the SMP foam was done before and after reticulation via low vacuum scanning electron microscopy (LV-SEM) using a NeoScope JCM-5000 (Jeol USA, Inc., Peabody, Mass.).

1.7. Mechanical Characterization of Foam

Mechanical testing of SMP foam was performed in compression mode according to ASTM D1621-10 Standard Test Method for Compressive Properties of Rigid Cellular Plastics using the Instron load frame with a 500N load cell at ambient laboratory temperatures 23±2° C., as specified within the text. Cylindrical samples 25.4 mm in diameter by 25.4 mm tall of both the non-reticulated and reticulated (chemically etched or not etched) foams were prepared. These samples were frozen in a −80° C. freezer overnight and subsequently lyophilized for 24 hours prior to mechanical testing. To assess the effects of pin mass, uni-axial vs. tri-axial reticulation, and chemical etching, nine different reticulation schemes (including a non-reticulated control) were investigated as outlined in Table 1 (shown above). Five (5) samples were tested for each scheme. Table 1 shows reticulation schemes employed for mechanical testing of foams.

1.8. Permeability Measurements

The nine cases of reticulation and etching, having varying densities were measured in triplicate. Each sample was evacuated overnight to remove air bubbles from the samples and was then placed within the chamber of a flow loop. The pressure drop across the foam was measured at various flow rates to determine the permeability. The flow rates measured ranged from 0 to 850 ml/min, or Darcy velocities between 0 to 0.071 m/s for each of the samples. Due to the range of pressures measured, three types of pressure transducers were used for these measurements: 1) 2,482 Pa differential pressure transducer (model # PX409-10WDWUV) 0.08% of range accuracy (Omega Engineering, Inc., Stamford, Conn.), 2) 17,240 Pa differential pressure transducer (model # PX409-2.5WDWUV) 0.08% of range accuracy, (Omega Engineering, Inc., Stamford, Conn.) and 3) two 206,800 Pa absolute membrane pressure transducers (model PXM42MG7-400MBARGV) 0.25% of range accuracy (Omega Engineering, Inc., Stamford, Conn.).

The reticulated samples were measured with the 2,482 Pa transducer until the differential pressure exceeded the maximum pressure of the transducer in the higher flow rates. Once the maximum differential pressure exceeded the capabilities of the first transducer, the measurements were recorded and read by the 17,240 Pa transducer. As the flow rates decreased on the second half of data acquisition, the data was the acquired from the more sensitive of the measurements available once the transducer was in the proper range of pressures. The set of 206,800 Pa transducers were used to measure the differential pressure of non-reticulated and non-etched control samples. In addition to the pressure transducers, a set of two rigid tubes were fashioned as a water manometer and a set of digital 206,800 Pa pressure gauges (Dwyer Instruments, Michigan City, Ind.) (Model: DPGWB-06) with 0.01 of range resolution, were used to determine the maximum pressure differential of the highest flow prior to measurement with the transducers (FIG. 5).

The pump consisted of a Verderflex® Smart, (Verderflex, England, U.K.) L20 series, peristaltic pump equipped with a non-standard six head roller on an isolated cart, for reduction of pulse within the system. In addition to the six head roller, 20 feet of large diameter (12.7 mm ID and 15.875 mm OD) flexible silicone tubing was placed after the pump just before five pulse dampeners. After the pulse dampeners, there was an additional 12 feet of semi-rigid flexible tubing (12.7 mm ID and 19.1 mm OD) and subsequently ten feet of rigid tubing (15.875 mm ID and 19.05 mm OD) before the pressure chamber. A flow meter probe, attached to a small animal blood flow meter (model number T206) (Transonic Inc., Ithaca, N.Y.) was placed after the five pulse dampeners to quantify the pulse within the system and for flow rate measurements. In an effort to further reduce the pulse of the system seen by the sample, the tank was also isolated on its own cart.

From these measurements the porous media properties were calculated using the Forchheimer-Hazen-Dupuit-Darcy (FHDD) equation: $-\partial P/\partial x = (\mu/K)v_o + \rho C v_o^2$, where the pressure gradient, $-\partial P/\partial x$, is along the sample in the direction of flow (Pa/m), $\mu$ is the dynamic viscosity of the fluid (Pa·s), K is the intrinsic permeability of the sample ($m^2$), $v_0$ is the Darcy velocity (average velocity or flow rate, Q, divided by cross-sectional area, A of the sample) (m/s), $\rho$ is the density of the fluid (kg/m$^3$), and C is the form factor of the sample ($m^{-1}$). Permeability is a geometric parameter of the foam and represents the loss in pressure across a sample due to viscous losses, or the coefficient of viscous flow resistance. Permeability is inversely proportional to the surface area of the foam in contact with the fluid. Form factor is also a geometric parameter of the foam and represents the losses in pressure across the sample due to inertial losses, or the coefficient of inertial flow resistance. Form factor is proportional to the projected cross sectional surface area of the foam perpendicular to the flow. These two coefficients represent the forces acting against the motion of fluid flow through the porous media. At low velocities, the viscous forces dominate. While, in higher velocities the inertial losses dominate. Calculated C and K values were reported for three samples of each case measured using water as the fluid.

1.9. In Vivo Vascular Occlusion Assessment

Uni-axial and tri-axial reticulated SMP foam samples were cut into 20-30 mm long cylindrical samples using a 10mm diameter biopsy punch. The samples were pre-conditioned by radially compressing to 1 mm diameter using a SC250 stent crimper (Machine Solutions Inc.®, Flagstaff, Ariz.) at 97° C. and heated to expand to their original shape. The SMP foam cylinders were then chemically etched, rinsed, and cleaned. The samples were dried in vacuum and stored in an air-tight container with desiccant. The cylindrical samples were cut to 8 mm diameter using fine-tip scissors and 10 mm long using a razor blade. Samples were then radially compressed to the minimum diameter of approximately 1 mm using the stent crimper at 97° C., cooled under compression to maintain the compressed shape, and stored in an air-tight container with desiccant until implantation in vivo.

Six (6) devices (3 uni-axial and 3 tri-axial reticulated using 1 g pins and etching) were successfully deployed into multiple hind limb vessels of a three month old, 25 kg pig. Angiography performed prior to implantation of the VODs indicated the diameters of the vessels were on average 2.6 mm in diameter, which was smaller than the 8-mm diameter of the uncompressed VODs; therefore, the devices were able to expand to approximately 33% of their original diameter. A 5F catheter, 0.055" inner diameter, was navigated to the implant site using a 0.035" guidewire. The compressed foam VOD was submerged in room temperature saline for 2-5 minutes and then submerged in 32° C. saline for 3-5 seconds. The device was placed inside the catheter for 5 minutes to allow the foam to begin expanding and then pushed out of the catheter using the 0.035" guidewire. This procedure resulted in expansion of the foam immediately as it emerged out of the catheter as shown in a preliminary benchtop in vitro demonstration. Contrast enhanced fluoroscopy was used to determine when the device had been deployed, by observing the location of the guide wire and if possible a lack of contrast agent in the vessel. After delivery into the vessel, the device expanded to its primary shape and subsequently blocked the vessel. We defined vessel occlusion time as the time after device delivery until injected contrast agent ceased to flow through or past the device; at that point clotting is likely to have occurred. Vessel occlusion time was determined via iodinated contrast injections visualized with angiography 45 seconds after deployment and then at 30 second intervals thereafter. Average occlusion times were reported.

2. Results and Discussion

2.1. Nitinol Pin Properties

From the six samples tested it was determined that the average Young's modulus of the nitinol wire was 58.62±0.93 GPa. From this data, the buckling load for different pin lengths was calculated. The buckling load for the 50-mm-long nitinol pins is estimated to be 0.5 g.

2.2. Mechanical Reticulation

The average and median mechanical load necessary to puncture a single membrane was determined to be 2.07±2.23 grams and 1.27 grams in the axial direction and 1.13±1.09 grams and 0.80 grams in the trans-axial direction respectively. Due to the range of measurements, large standard deviation and overlapping data a Wilcoxon Mann test was used to evaluate the difference between the two data sets. The Wilcoxon Mann test resulted in a P_TwoTail value of 0.00252858, which indicated that the two data sets were not the same. Buckling of the nitinol pins may occur based on these measurements, which could influence the reticulation path (and, hence, the number of punctured membranes) as they penetrate through the foam. Friction during penetration though the foam was estimated to be 0.12 g/mm. Spikes in the data are interactions between the nitinol tip and either a membrane or a strut of the SMP foam, and were intentionally ignored for the friction estimate. However, the spikes generally exceeded the estimated buckling load of the nitinol pins, further suggesting that buckling can occur during reticulation.

2.3. Effect of Reticulation of Foam Mechanical Properties

The foams reticulated according to Table 1 are shown in FIG. 5. The non-reticulated control foam had an average elastic modulus of approximately $2.65 \times 10^5$ Pa. Reticulation reduced the modulus, with the tri-axial reticulated foams having the lowest moduli. The more extensive disruption of the cell membranes caused by reticulation in multiple axes resulted in higher reduction of the modulus. Closer inspection of the data shows that chemical etching of the uni-axial reticulated foam increased the modulus, while the tri-axial reticulated foams showed a slight decrease in modulus after chemical etching. In both the axial and tri-axial cases, the modulus was higher when 2 gram pins were used for axial reticulation compared to the use of 1 g pins. Following the trend in modulus, the non-reticulated foam had the highest stress plateau before densification, followed by the uni-axial and finally the tri-axial reticulated foams.

2.4. Permeability of Samples

The measurements and FHDD algorithm fitted curves of the non-reticulated control samples were determined. Permeability (K) and form factor (C) of each sample that was fitted with the FHDD equation was calculated from the pressure gradient.

Form factor and permeability were plotted versus the idealized volume of material removed per cubic meter of solid polymer via mechanical reticulation, where the idealized volume of material removed was determined from the volume of the nitinol pins multiplied by the punch pattern. The sum of the volume of the nitinol pins was subtracted from a 1 $m^3$ solid volume of polymer for the different reticulation patterns. Non-reticulated control samples correspond to 0.0 $m^3$, uni-axial is 0.126 $m^3$, tri-axial is 0.286 $m^3$ of material removed per $m^3$. It was shown that all reticulated samples were an order of magnitude higher than the control samples in permeability and an order of magnitude lower in form factor.

2.5. In Vivo Vascular Occlusion

The uni-axial reticulated foam had an average occlusion time of 90±11 s and the tri-axial reticulated foam had an average occlusion time of 128±77 s. On average the uni-axial reticulated foam induced faster occlusion that the tri-axial reticulated foam. This result is not unexpected since blood flow is likely impeded more by the less reticulated foam, potentially resulting in more rapid clotting.

3. Conclusions

SMP foams are biocompatible in vivo, when implanted into a porcine aneurysm model. Though excellent healing was observed, these foams possessed a predominantly closed-cell structure, which likely limits the amount of blood flow allowed to percolate through the material and may delay or inhibit optimal healing in vivo. Reticulation may enhance application of these materials as an aneurysm filling or other vascular occlusion device. Some embodiments address mechanical reticulation of these foams for vascular occlusion. These mechanically reticulated devices had membranes that were punctured, rather than completely removed. For example, FIG. 6(A) includes a close up of the "10X top" "1 g, no etch" "Uni-axial" figure of FIG. 5 and FIG. 6(B) includes a close up of the "10X top" "2 g, no etch"

Figure 6A:
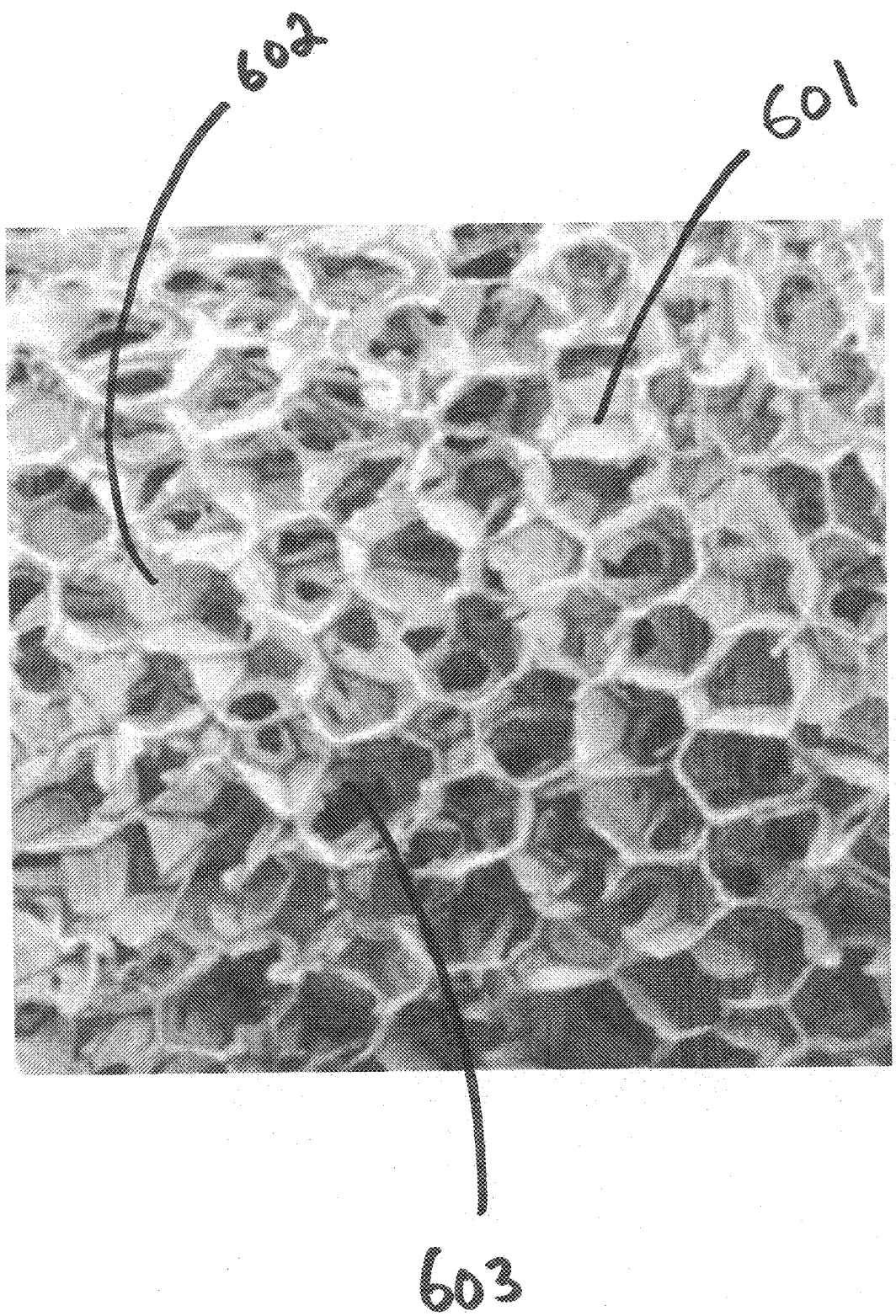
FIG. 6(A) includes a close up of the "10X top" "1 g, no etch" "Uni-axial" figure of FIG. 5.
Figure 6B:
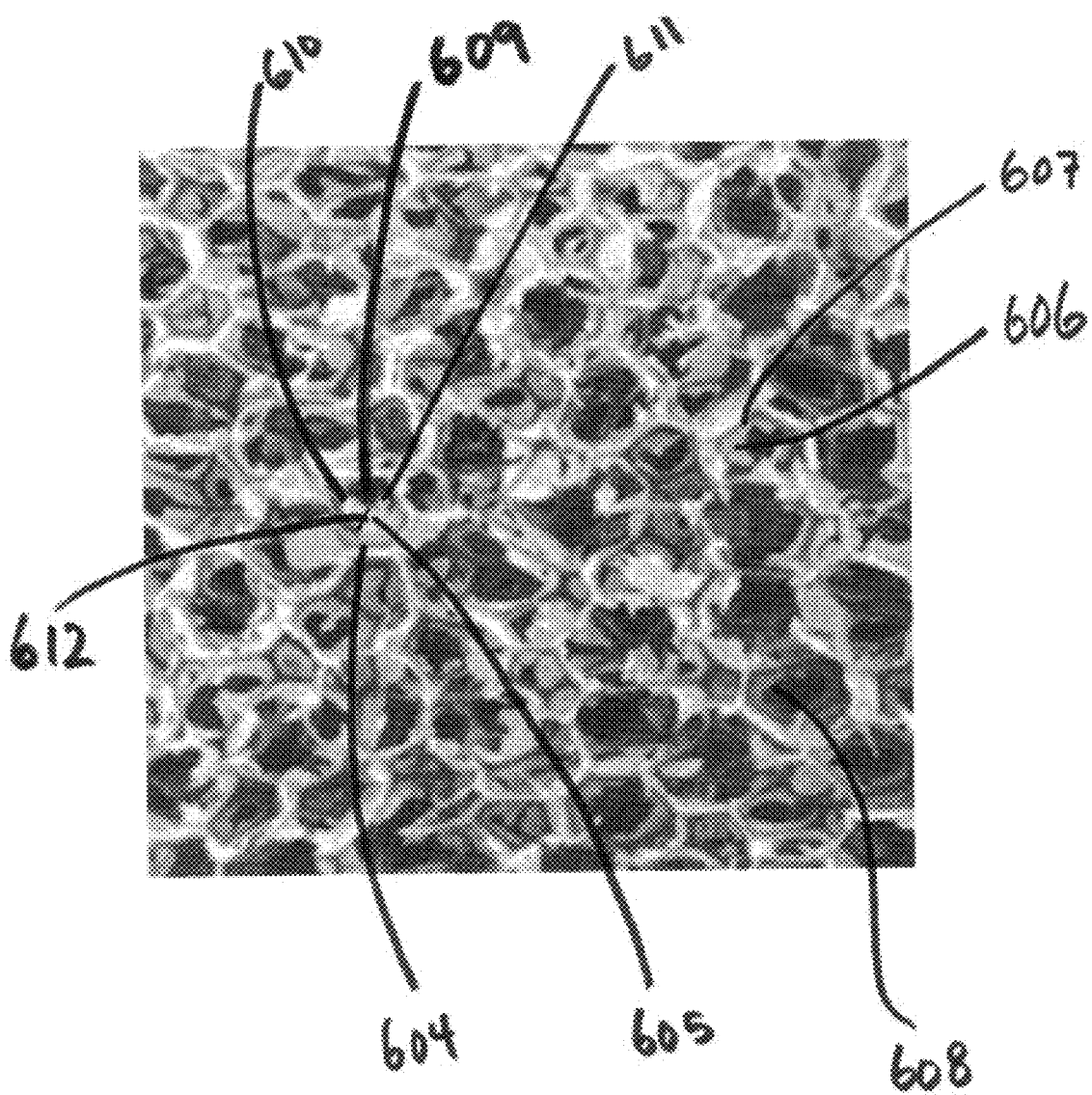
FIG. 6(B) includes a close up of the "10X top" "2 g, no etch" "Uni-axial" figure of FIG. 5.
Figure 6C:
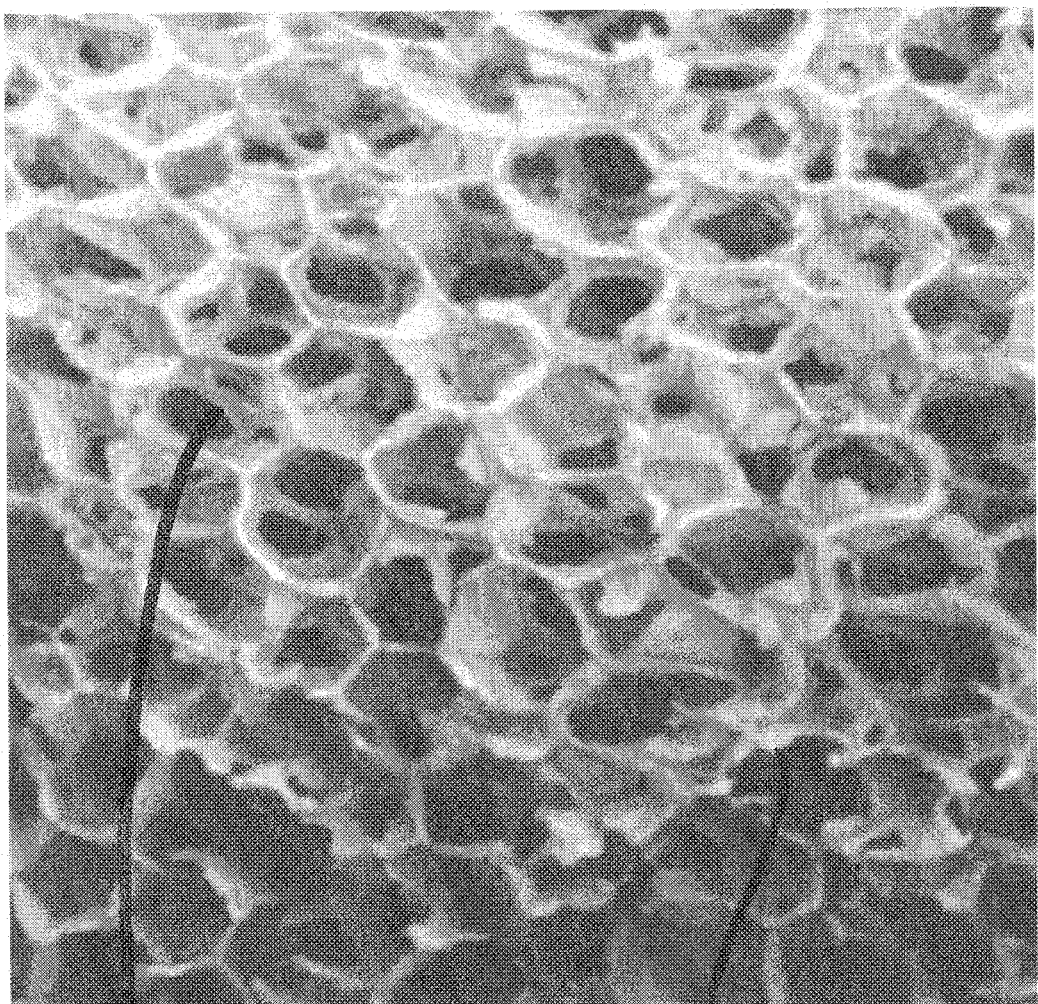
FIG. 6(C) includes a close up of the "10X top" "1 g, etch" "Uni-axial" figure of FIG. 5.

"Uni-axial" figure of FIG. 5. FIG. 6(C) includes a close up of the "10X top" "1 g, etch" "Uni-axial" figure of FIG. 5. The non-etched FIGS. 6(A) and 6(B) show punctured membranes 603, 605, 606, 608 among struts 601, 604, 607. The punctured membranes are identified by their irregular, jagged, ruptured perimeters as opposed to the smooth, etched perimeter of membrane 609' of FIG. 6(C). Membrane protuberence 610 is shown to address a membrane that is jagged merely because it was cut when preparing the foam for imaging and is along the outer perimeter of the foam (as opposed to membranes 603, 605, 606, 608 that are not on the outer perimeter of the foam). Membrane 602 is not punctured. The shredded remnants of membranes 603, 605, 606, 608 increase the ability to act as an occlusion device due to greater surface area in contact with blood, relative to completely reticulated membranes, or foams that have open windows between individual pore cells.

An embodiment includes a method for non-destructive mechanical reticulation of ultra low density SMP foam by using a gravity-driven floating nitinol pin array coupled with vibratory agitation of the foam. Appropriate pin masses and agitation amplitude were identified to enable the desired level of reticulation. Embodiments focus on mechanical reticulation in different axes, versus changing the pin density of the array, to adjust the level of reticulation, and investigated chemical etching of the materials post reticulation.

Visually, there appeared to be a tradeoff of puncturing membranes, or membrane damage created as a function of mass, by down selecting to two and one gram pins for the preliminary detailed studies in the axial direction of puncture. In other words, the channels of the two gram pins appear to be less tortuous compared to the one gram pins when punched parallel to the axis of foaming, and therefore make a more direct path during reticulation. The less direct path, taken by the lower mass pins during reticulation, results in a less permeable sample. This is most likely due to the increase in surface area for which the fluid must interact with during the measurements of the pressure differential across the samples. Permeability measurements appear to confirm this statement as was evident by the majority of the two gram reticulated samples measured having a higher permeability, K values and lower form factor, C values.

The data for the permeability shows that uni-axial and tri-axial reticulation increased the permeability for all cases compared to the control samples tested. An embodiment of the mechanical reticulation system is non-destructive and leave most struts intact. In order to achieve this goal some of the pins do not reticulate the entire thickness for every instance of reticulation. The nitinol pins also deflect as they puncture the materials, making the pathways diverge away from a straight trajectory. Both of these results would cause variation in the amount of removal of membranes from sample to sample.

Overall, mechanical reticulation resulted in a reduced elastic modulus, but did not impede shape memory behavior as demonstrated by the in vitro delivery and in vivo occlusion tests. The modulus was lower for foams reticulated in multiple axes compared to a single axis. Supplemental chemical etching was not mechanically detrimental and for the axial cases tended to slightly increase the elastic modulus. Although the mechanical properties of the foams were decreased by all reticulation methods, the expansion in vivo was not affected. This is most likely due to the strong shape memory behavior and high stress recovery of these highly cross-linked polyurethane materials. In other words, the mechanical properties of the bulk material were decreased by the reticulation methods, due to the loss in shear walls of the individual pores, but the ability of the structures to regain their primary shape via shape memory recovery is not greatly affected unless there is damage to many struts of the foam (thereby indicating struts have a primary structural role while membranes do not and instead function more to separate cells from one another). The shape memory properties should remain intact due to the struts, or main architecture of the material remaining unaffected by the reticulation, even if they are slightly less in recovery strength or take longer to recover. In addition, when the material is exposed to an aqueous environment in vivo, the materials may also be absorbing water from the environment and this may aid in the expansion to fill the vessel, and this effect may surpass any loss in mechanical properties due to reticulation.

The reticulated VODs were capable of achieving rapid vascular occlusion in an in vivo porcine model, indicating that SMP foam could be used as a device not only to fill aneurysms, but to also occlude patent vessels under arterial pressure. It was shown that on average the less reticulated the VOD, the faster the occlusion time.

The following examples pertain to further embodiments.

Example 1 includes a device to controllably reticulate polymeric-based closed cell foams comprising: an array, capable of containing a plurality of needles; and a shaker, capable of receiving a sample of a polymeric-based closed cell foam, the array configured so that the plurality of needles puncture membranes of the sample of the polymeric-based closed cell foam in at least one axis due, at least in part, to an oscillation of the shaker and a motion of the plurality of needles of the array into the sample of the polymeric-based closed cell foam.

Example 2 includes the device of example 1, wherein the needles, comprising the plurality of needles, are comprised of a nitinol alloy.

Example 3 includes the device of example 1, wherein the needles, comprising the plurality of needles, are comprised of an alloy capable of puncturing membranes of the sample of the polymeric-based closed cell foam due, at least in part, to an application of a force on the plurality of needles.

Example 4 includes the device of example 3, wherein the application of the force on the plurality of needles is gravity.

Example 5 includes the device of example 1, wherein the array is configured so that the plurality of needles puncture membranes of the sample of the polymeric-based closed cell foam in three axes.

Example 6 includes the device of example 1, wherein the array is comprised of low-friction channels, each channel capable of receiving a needle.

Example 7 includes the device of example 1, wherein the sample of the polymeric based closed cell foam is comprised of a SMP foam.

Example 8 includes the device of example 1, wherein the shaker, capable of receiving the sample of the polymeric-based closed cell foam, is configured to receive instructions to vary the rate of the oscillations of the shaker, thereby inducing a deeper penetration of the plurality of needles of the array into the sample of the polymeric-based closed cell foam.

Example 9 includes the device of example 1, wherein the quantity of membranes of the sample of the polymeric based closed cell foam that are punctured varies depending, at least in part, on the oscillations of the shaker.

Example 10 includes the device of example 1, wherein the array, capable of containing a plurality of needles, is suspended from an apparatus, configured to move in controlled-stepwise fashion, for a stepwise reticulation of the sample of the polymeric-based closed cell foam.

Example 11 includes the device of example 10, wherein the apparatus, configured to move in a controlled-stepwise fashion, for a stepwise reticulation of the sample of the polymeric-based closed cell foam can be any of a milling machine, automated XYZ stage, or similar apparatus.

Example 12 includes a method to reticulate polymeric-based closed cell foams comprising: removing membranes of a polymeric-based closed cell foam through mechanical agitation of the polymeric-based closed cell foam in at least one axis.

Example 13 includes the method of example 12, wherein said removing membranes of a polymeric-based closed cell foam through mechanical agitation of the polymeric-based closed cell foam in at least one axis further comprises piercing membranes of the polymeric-based closed cell foam.

Example 14 includes the method of example 12, wherein said removing membranes of a polymeric-based closed cell foam through mechanical agitation of the polymeric-based closed cell foam in at least one axis further comprises a controlled mechanical agitation of the polymeric-based closed cell foam to controllably vary the quantity of membranes of the polymeric-based closed cell foam removed.

Example 15 includes the method of example 12, wherein said removing membranes of a polymeric-based closed cell foam through mechanical agitation of the polymeric-based closed cell foam further comprises removing membranes of the polymeric-based closed cell foam in three axes.

Example 16 includes the method of example 15, wherein said removing membranes of the polymeric-based closed cell foam in three axes further comprises: puncturing membranes of the polymeric-based closed cell foam in a first axis; rotating the polymeric-based closed cell foam; puncturing the polymeric-based closed cell foam in a second axis; rotating the polymeric-based closed cell foam; and puncturing the polymeric-based closed cell foam in a third axis.

Example 17 includes a method to reticulate polymeric-based closed cell foams, using the device of example one, comprising: receiving a sample of a polymeric-based closed cell foam on the shaker of the device of example one; agitating the sample of the polymeric-based closed cell foam by causing the shaker of the device of example one to oscillate vertically thereby inducing the plurality of needles of the array of the device of example one to move towards the sample of the polymeric-based closed cell foam, such motion due, at least in part, to gravity; and adjusting a rate of the vertical oscillation of the shaker of the device of example one to cause the plurality of needles of the array of the device of example one to penetrate a thickness of the sample of the polymeric-based closed cell foam.

Example 1a includes a device, which reticulates foams via mechanical means.

Example 2a includes the device of Example 1a where the reticulation is performed with needle-like objects.

Example 3a includes the method of Example 2a where force is applied via the needle-like objects to compromise the membranes but maintain the integrity of the foam struts.

Example 4a includes the method of Example 3a where the force applied to compromise the membranes comes from gravity.

Example 5a includes the method of Example 4a where the force of gravity is controlled by the weight of the needle-like objects used to compromise the membranes.

Example 6a includes the method of Example 2a where vibration of the foam facilitates motion of the needle-like objects into un-compromised membranes.

Example 7a includes the method of Example 6a where the vibrations occur in multiple dimensions.

Example 8a includes the device of Example 1a where the percentage of total membranes compromised can be controlled.

Example 9a includes the method of Example 8a where the percentage of membranes compromised is controlled by step spacing.

Example 10a includes the device of Example 1a where reticulation is performed in a single or multiple dimensions.

Example 11a includes the device of Example 10a used to control the directionality of flow into the material such that permeation of fluid into the material is allowed in selected directions and prevented in other directions.

Example 12a includes the method of Example 1a where the reticulation system can be tuned to produce different mechanical properties in foam based on the percentage of membranes or struts compromised.

Example 13a includes the device of Example 1a used to reticulate foams in medical devices.

Example 14a includes the device of Example 13a where the medical device has an embolic application.

Example 15a includes the device of Example 14a where the percentage of membranes compromised is used to control the rate of embolization.

Example 1b includes a system comprising: a polyurethane shape memory polymer (SMP) foam having first and second states; first and second cells, included in the SMP foam, which directly contact each other; wherein (a)(i) the first and second cells share and directly contact a ring of struts that provide structural support for the first and second cells, (a)(ii) a membrane directly contacts the ring of struts, and (a)(iii) the membrane is partially reticulated but not fully reticulated; wherein the partially reticulated membrane includes: (b)(i) a void that forms a path configured to allow fluid to flow between the first and second cells, (b)(ii) an interface, between the partially reticulated membrane and the void, which is rough and uneven.

While a polyurethane SMP foam is addressed in this example other embodiments are not so limited and relate more generally to closed cell polymer based foams.

Dashed line 411 in FIG. 4 illustrates a junction or interface between a strut 412 and a membrane 413. The strut is primarily responsible for elasticity (Young's modulus) and shape memory characteristics. In contrast, membrane 413 has a minimal contribution to the elasticity and shape memory of the foam when compared to the strut. Cells 407, 408 directly contact each other and share a ring of struts, two of which are struts 409, 410. Membrane 405 directly contacts struts 409, 410. Membrane 405 is not reticulated but membrane 605 (FIG. 6) is partially reticulated. In FIG. 6(B), a void 609 is between two flaps or protuberances 610, 611.

Another version of Example 1b includes a system comprising: a polyurethane shape memory polymer (SMP) foam having first and second states; first and second cells, included in the SMP foam, which directly contact each other; wherein (a)(i) the first and second cells share and directly contact at least one strut that provides structural support for the first and second cells, (a)(ii) a membrane directly contacts the at least one strut, and (a)(iii) the membrane is partially reticulated but not fully reticulated; wherein the partially reticulated membrane includes: (b)(i) a void that forms a path configured to allow fluid to flow between the first and second cells, (b)(ii) an interface, between the partially reticulated membrane and the void, which is rough and uneven.

Example 2b includes the system of example 1b wherein the interface is not chemically etched.

For instance, membrane 609' of FIG. 6(C) is chemically etched (in contrast to membranes 605, 608 of FIG. 6(B)).

Example 3b includes the system of example 1b wherein the SMP foam includes cells, including the first and second cells, which are anisotropic in shape and have unequal major and minor axes.

For instance, see major axis 414 and minor axis 415 of FIG. 4(B). The direction of foam growth for the foam of FIG. 4(B) is generally parallel to axis 414.

Example 4b includes the system of example 3b, wherein: the ring of struts define an outer perimeter of the membrane and the void defines an inner perimeter of the membrane; an outer membrane area for the membrane is an area bounded by the outer perimeter defining an area of the membrane before reticulation; a void area is an area bounded by the inner perimeter defining an area of the void; and the void area is between 25% and 75% of the outer membrane area.

For instance, the "outer membrane area" in FIG. 4(B) would be the area of membrane 404. If membrane 404 were reticulated and have a void, the "void area" would be the area of that reticulation induced void. With a void area between 25% and 75% of the outer membrane area, a membrane would not be fully reticulated (where the percentage would be, for example, 99% or higher) or unreticulated (where the percentage would be 0%). Other ranges include, for example, between 15% and 85% and between 35% and 65%.

Example 5b includes the system of example 4b, wherein: the interface defines a protuberance of the membrane that protrudes away from the ring of struts and toward a central region of the void; and the ring of struts form a complete ring that is unbroken.

Example 6b includes the system of example 5b, wherein the protuberance includes a flap that is configured to rotate along an axis at least 25 degrees into the first cell and at least 25 degrees into the second cell in response to fluid flow between the first and second cells.

For instance, see axis 612 which allows flap/protuberence 610 to move back and forth (into and out of the page) with fluid flow through void 609. Void 609 allows fluid flow to cells on either side of membrane 605. An interface or junction between a rupture membrane and a void is rough and uneven, as seen at membrane 608 and 605. While the flaps/protuberences 610, 611 may have smooth edges the flaps themselves provide a rough and uneven contour to membrane 605. This is in contrast to a smooth and even contour of, for example, membrane 609' of FIG. 6(C). Further, note that membrane 609' of FIG. 6(C) includes no such flap and has no axis allowing a protuberance to flow in and out adjacent cells.

Example 7b includes the system of example 6b, wherein the SMP foam comprises: a first path, configured to allow fluid to flow between at least 5 cells, formed along an axis generally parallel to the major axis; and a second path, configured to allow fluid to flow between an additional at least 5 cells, formed along an additional axis generally parallel to the major axis; wherein a third axis, generally parallel to the minor axis, intersects at least one of the at least 5 cells and at least one of the additional at least 5 cells.

Such paths may include paths formed by two adjacent needles that, based on superelasticity of the needles and vibrations from the vibrator, take tortuous paths through the foam making paths that are generally parallel to one another. An axis, generally orthogonal to these paths, would intersect cells from both paths.

Example 8b includes the system of example 6b, wherein: at least one portion of the ring of struts directly contacts a third cell; the at least one portion of the ring of struts is between the third cell and the membrane; and a second membrane separates the first and third cells from each other.

For instance, strut confluence 401 shows an intersection between 3 cells. Thus, a ring including strut portion 402 (contacting 2 cells) would also include a portion 401 that contacts an additional cell.

Another version of example 8 includes the system of example 6b, wherein: at least one portion of the ring of struts directly contacts a third cell; the at least one portion of the ring of struts is between the third cell and the membrane; a second membrane separates the first and third cells from each other; and a third membrane separates the second and third cells from each other.

Example 9b includes the system of example 8b, wherein at least one strut of the ring of struts includes a generally delta shaped cross-section.

See, for instance, area 401 of FIG. 4(B). While FIGS. 4(A) and (B) are sometimes used to explain concepts for embodiments with reticulated cells, even though the cells of FIGS. 4(A) and (B) are not reticulated, the concepts are not changed. In other words, a portion of a membrane intersects a strut in the same way regardless of whether a portion of that membrane is or is not reticulated.

Example 10b includes the system of example 8b comprising: an additional polyurethane SMP foam having first and second states; additional first and second cells, included in the additional SMP foam, which directly contact each other; wherein (a)(i) the additional first and second cells share an additional ring of struts that provide structural support for the additional first and second cells, (a)(ii) an additional membrane directly contacts the additional ring of struts, and (a)(iii) the additional membrane is partially reticulated and not fully reticulated; wherein the partially reticulated additional membrane includes: (b)(i) an additional void that forms an additional path configured to allow fluid to flow between the additional first and second cells, (b)(ii) an additional interface, between the partially reticulated additional membrane and the additional void, which is rough and uneven; wherein the SMP foam and the additional SMP foam include identical chemical compositions; wherein the SMP foam is more reticulated than the additional SMP foam; wherein the SMP foam is at least 10% more permeable than the additional SMP foam in response to the SMP foam being more reticulated than the additional SMP foam.

Thus, reticulation may be used to change permeability while keeping the chemistry of the foams the same. In other words, both foams may have the chemistry of example 11b but still have different porosity due to varying amounts of reticulation.

Example 11b includes the apparatus of example 8b, wherein the SMP foam includes N,N,N',N'-tetrakis (2-hydroxypropyl) ethylenediamine (HPED), triethanolamine (TEA), and hexamethylene diisocyanate (HDI) with TEA contributing a higher molar ratio of hydroxyl groups than HPED.

Example 12b includes the system of example 8b, wherein the SMP foam includes N,N,N',N'-tetrakis (2-hydroxypropyl) ethylenediamine (HPED), triethanolamine (TEA), and trimethylhexamethylenediamine (TMHDI) with HPED contributing a higher molar ratio of hydroxyl groups than TEA.

Example 13b includes the system of example 8b, wherein the SMP foam includes N,N,N',N'-tetrakis (2-hydroxypropyl) ethylenediamine (HPED), Glycerol, pentanediol, and hexamethylene diisocyanate (HDI).

Example 14b includes the system of example 8b wherein a majority of reticulated membranes of the SMP foam include voids and interfaces with those voids and the interfaces are rough and uneven.

For instance, Example 1b discusses a few cells for illustration but an embodiment includes a foam with many cells partially mechanically reticulated, such as those foams of FIGS. 6(A) and 6(B).

Example 15b includes the system of example 14b, wherein the interfaces of the majority of the reticulated membranes define protuberances that protrude toward central regions of the voids of the majority of the reticulated membranes.

Example 16b includes a method comprising: coupling a polymeric-based closed cell foam to a vibrator, wherein (a)(i) the foam includes first and second cells that share a ring of struts that provide structural support for the first and second cells, and (a)(ii) a membrane directly contacts the ring of struts; coupling an array of needles to the foam; vibrating the foam with the vibrator; in response to vibrating the foam, (b)(i) contacting at least one of the needles against at least one of the struts, (b)(ii) decoupling the at least one needle from the at least one strut and then coupling the at least one needle to the membrane, and (b)(iii) puncturing the membrane with the at least one needle and then puncturing additional membranes, also included in the foam, with the at least one needle to form a contiguous path configured to allow fluid to flow through the reticulated membranes.

For instance, the vibrations and use of gravity give a needle that contacts a strut an opportunity to bounce or vibrate off that strut and instead land on a membrane that has less resistance than the strut. The needle may take the "path of least resistance" as it matriculates through the foam, thereby creating paths that increase porosity.

Example 17b includes the method of example 16b comprising: coupling an additional polymeric-based closed cell foam to the vibrator, wherein (a)(i) the additional foam includes additional first and second cells that share an additional ring of struts that provide structural support for the additional first and second cells, and (a)(ii) an additional membrane directly contacts the additional ring of struts; coupling an additional array of needles to the additional foam; vibrating the additional foam with the vibrator; in response to vibrating the additional foam, (b)(i) contacting at least one of the additional needles against at least one of the additional struts, (b)(ii) decoupling the at least one additional needle from the at least one additional strut and then coupling the at least one additional needle to the additional membrane, and (b)(iii) puncturing the additional membrane with the at least one additional needle; wherein the foam and the additional foam have different chemical compositions; wherein the array of needles includes a first number of needle systems having a first collective mass and the additional array of needles includes a second number of needle system, equal to the first number of needles, having a second collective mass unequal to the first collective mass.

Thus, for foams of different chemistries such as the foams of examples 11b and 12b a user may elect to use differently weight needle systems to arrive at a desired porosity. Instead or in addition to changing masses of needle systems, a user may vary the vibration by changing oscillation frequency and/or amplitude. Also, a "needle system" may include not only the needle but the block 321 as well. Such blocks may have different masses even though the needle portions 322 have the same masses. Also, as used herein, a "needle" includes a slender pointed instrument for piercing a material.

Example 18b includes the method of example 17b, wherein: vibrating the foam with the vibrator includes oscillating the foam at at least one of a first frequency and a first amplitude; vibrating the additional foam with the vibrator includes oscillating the additional foam at at least one of a second frequency and a second amplitude; at least one of (a) the first and second frequencies are unequal, and (b) at least one of the first and second amplitudes are unequal.

Embodiments allow for varying frequency and/or amplitude while keeping needle system mass the same. Also, embodiments allow for different numbers of needles to be used in differing arrays or different patterns of needles. For example, a user may wish one end of a foam to be more reticulated than another end of the same foam. Accordingly, the array of needles may have more needles in one area than another. For example, a VOD may include a portion of the foam meant for a neck of an aneurysm to have a first porosity and another portion of the foam meant for the main body of the aneurysm to have a second porosity unequal to the first porosity. The same could be true for, as an example, insulation material that may have a lower porosity for edge portions of a foam that interface weather but a higher porosity for internal portions of the foam. Additionally, a gradient in mechanical reticulation could alter the compressive properties of the foam for variable stiffness in shock absorbing applications.

Example 19b includes the method of example 16b comprising: coupling an additional polymeric-based closed cell foam to the vibrator, wherein (a)(i) the additional foam includes additional first and second cells that share an additional ring of struts that provide structural support for the additional first and second cells, and (a)(ii) an additional membrane directly contacts the additional ring of struts; coupling an additional array of needles to the additional foam; vibrating the additional foam with the vibrator; in response to vibrating the additional foam, (b)(i) contacting at least one of the additional needles against at least one of the additional struts, (b)(ii) decoupling the at least one additional needle from the at least one additional strut and then coupling the at least one additional needle to the additional membrane, and (b)(iii) puncturing the additional membrane with the at least one additional needle; wherein the foam and the additional foam have equivalent chemical compositions; wherein the array of needles includes a first number of needle systems having a first collective mass and the additional array of needles includes a second number of needle systems, equal to the first number of needles, having a second collective mass unequal to the first collective mass; wherein the foam is at least 10% more permeable than the additional foam.

Thus, changing the masses of needle systems may adjust porosity without having to adjust chemistry of the foam.

Example 20b includes the method of example 16b, wherein the needles are superelastic when contacting at least one of the needles against at least one of the struts.

Superelasticity may also be referred to pseudoelasticity. As used herein, it is a property unique to shape memory alloys where they can reversibly deform to strains as high as 10%. This deformation characteristic does not require a change in temperature (like the shape memory effect), but the material needs to be above the transformation temperature to have superelasticity.

Example 21b includes the method of example 16b, wherein puncturing the membrane with the at least one needle includes puncturing the membrane with the at least one needle in response to gravity.

Thus, instead of driving the needles through the foam (in a manner similar to how a drill press drives the drill through a material) (which could result in strut damage), vibration and gravity allows for an easier less strut destructive path through the foam. Also, in some embodiments the substrate that includes channels for pins has channels that are sized and include a material such that the needles "free float" and free to drop through the foam due to gravity and vibration.

Example 22b includes the method of example 16b comprising: coupling an additional polymeric-based closed cell foam to the vibrator, wherein (a)(i) the additional foam includes additional first and second cells that share an additional ring of struts that provide structural support for the additional first and second cells, and (a)(ii) an additional membrane directly contacts the additional ring of struts; coupling an additional array of needles to the additional foam; vibrating the additional foam with the vibrator; in response to vibrating the additional foam, (b)(i) contacting at least one of the additional needles against at least one of the additional struts, (b)(ii) decoupling the at least one additional needle from the at least one additional strut and then coupling the at least one additional needle to the additional membrane, and (b)(iii) puncturing the additional membrane with the at least one additional needle; wherein the foam and the additional foam have equivalent chemical compositions; wherein vibrating the foam with the vibrator includes oscillating the foam at at least one of a first frequency and a first amplitude; wherein vibrating the additional foam with the vibrator includes oscillating the additional foam at at least one of a second frequency and a second amplitude; wherein at least one of (a) the first and second frequencies are unequal, and (b) at least one of the first and second amplitudes are unequal.

Thus, foams with the same chemistries may have differing porosities based on using differing oscillatory factors for their respective reticulations.

Example 23b includes a system comprising: a vibrator; an array of needles that are superelastic at 75 degrees Fahrenheit; a substrate including a plurality of channels configured to receive the array of needles; wherein the vibrator, the array of needles, and the substrate are configured to: couple a polymeric-based closed cell foam to the vibrator, wherein (a)(i) the foam includes first and second cells that share a ring of struts that provide structural support for the first and second cells, and (a)(ii) a membrane directly contacts the ring of struts; couple the array of needles to the foam; vibrate the foam with the vibrator; in response to vibrating the foam, (b)(i) contact at least one of the needles against at least one of the struts, (b)(ii) decouple the at least one needle from the at least one strut and couple the at least one needle to the membrane, and (b)(iii) puncture the membrane with the at least one needle.

Thus, the needle systems may be superelastic to facilitate strut preservation while performing the reticulation at roughly room temperature. In an embodiment the needle system includes nitinol that has been heat treated so that it is superelastic at room temperature.

Example 24b includes the system of example 23b comprising an elevator to move the substrate towards and away from the vibrator.

Example 25b includes the system of example 23b comprising an additional array of needles, wherein: the plurality of channels are configured to receive the additional array of needles; and the vibrator, the additional array of needles, and the substrate are configured to: couple an additional polymeric-based closed cell foam to the vibrator, wherein (a)(i) the additional foam includes additional first and second cells that share an additional ring of struts that provide structural support for the additional first and second cells, and (a)(ii) an additional membrane directly contacts the additional ring of struts; couple the additional array of needles to the additional foam; vibrate the additional foam with the vibrator; in response to vibrating the additional foam, (b)(i) contact at least one of the additional needles against at least one of the additional struts, (b)(ii) decouple the at least one additional needle from the at least one additional strut and then couple the at least one additional needle to the additional membrane, and (b)(iii) puncture the additional membrane with the at least one additional needle; wherein the foam and the additional foam have different chemical compositions; wherein the array of needles includes a first number of needles having a first collective mass and the additional array of needles includes a second number of needles, equal to the first number of needles, having a second collective mass unequal to the first collective mass.

Example 26b includes the system of example 23b, wherein the vibrator is configured to oscillate at at least one of (a) a plurality of frequencies, and (b) a plurality of amplitudes.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:
1. A system comprising:
a polyurethane shape memory polymer (SMP) foam having first and second states;
first and second cells, included in the SMP foam, which directly contact each other;
wherein (a)(i) the first and second cells share and directly contact a ring of struts that provide structural support for the first and second cells, (a)(ii) a membrane directly contacts the ring of struts, and (a)(iii) the membrane is partially reticulated but not fully reticulated;
wherein the partially reticulated membrane includes: (b)(i) a void that forms a fluid path between the first and second cells, (b)(ii) an interface, between the partially reticulated membrane and the void, which is rough and uneven;
wherein the SMP foam includes a composition, the composition including at least one of: (c)(i) N,N,N',N'-tetrakis (2-hydroxypropyl) ethylenediamine (HPED), triethanolamine (TEA), and hexamethylene diisocyanate (HDI) with TEA contributing a higher molar ratio of hydroxyl groups than HPED; (c)(ii) HPED, TEA, and trimethylhexamethylenediamine (TMHDI) with HPED contributing a higher molar ratio of hydroxyl groups than TEA, or (c)(iii) HPED, glycerol, pentanediol, and HDI.

2. The system of claim 1 wherein the interface is not chemically etched.

3. The system of claim 1 wherein the SMP foam includes cells, including the first and second cells, which are anisotropic in shape and have unequal major and minor axes.

4. The system of claim 3, wherein:
the ring of struts defines an outer perimeter of the membrane and the void defines an inner perimeter of the membrane;
an outer membrane area for the membrane is an area bounded by the outer perimeter defining an area of the membrane before reticulation;
a void area is an area bounded by the inner perimeter defining an area of the void;
and the void area is between 25% and 75% of the outer membrane area.

5. The system of claim 4, wherein:
the interface defines a protuberance of the membrane that protrudes away from the ring of struts and toward a central region of the void; and
the ring of struts forms a complete ring that is unbroken.

6. The system of claim 5, wherein the protuberance includes a flap that rotates along an axis at least 25 degrees into the first cell and at least 25 degrees into the second cell in response to fluid flow between the first and second cells.

7. The system of claim 6, wherein the SMP foam comprises:
a first contiguous fluid path between at least 5 cells, formed along an axis generally parallel to a major axis of the foam; and
a second contiguous fluid path between an additional at least 5 cells, formed along an additional axis generally parallel to the major axis;
wherein a third axis, generally parallel to a minor axis of the foam, intersects at least one of the at least 5 cells and at least one of the additional at least 5 cells.

8. The system of claim 6, wherein:
at least one portion of the ring of struts directly contacts a third cell;
the at least one portion of the ring of struts is between the third cell and the membrane; and a second membrane separates the first and third cells from each other.

9. The system of claim 8, wherein at least one strut of the ring of struts includes a generally delta shaped cross-section.

10. The system of claim 8 comprising:
an additional polyurethane SMP foam having first and second states;
additional first and second cells, included in the additional SMP foam, which directly contact each other;
wherein (a)(i) the additional first and second cells share an additional ring of struts that provide structural support for the additional first and second cells, (a)(ii) an additional membrane directly contacts the additional ring of struts, and (a)(iii) the additional membrane is partially reticulated and not fully reticulated;
wherein the partially reticulated additional membrane includes: (b)(i) an additional void that forms an additional fluid path between the additional first and second cells, (b)(ii) an additional interface, between the partially reticulated additional membrane and the additional void, which is rough and uneven;
wherein the SMP foam and the additional SMP foam include identical chemical compositions;
wherein the SMP foam is more reticulated than the additional SMP foam;
wherein the SMP foam is at least 10% more permeable than the additional SMP foam in response to the SMP foam being more reticulated than the additional SMP foam;
wherein the SMP foam is separate from the additional SMP foam and is not uniform with the additional SMP foam.

11. The apparatus of claim 8, wherein the composition includes HPED, TEA, and HDI with TEA contributing a higher molar ratio of hydroxyl groups than HPED.

12. The system of claim 8, wherein the composition includes HPED, TEA, and TMHDI with HPED contributing a higher molar ratio of hydroxyl groups than TEA.

13. The system of claim 8, wherein the composition includes HPED, glycerol, pentanediol, and HDI.

14. The system of claim 8 wherein a majority of reticulated membranes of the SMP foam include voids and interfaces with those voids and the interfaces are rough and uneven.

15. The system of claim 14, wherein the interfaces of the majority of the reticulated membranes define protuberances that protrude toward central regions of the voids of the majority of the reticulated membranes.

16. A system comprising:
a polyurethane shape memory polymer (SMP) foam having first and second states;
first and second cells, included in the SMP foam, which directly contact each other;
wherein (a)(i) the first and second cells share and directly contact a ring of struts that provide structural support for the first and second cells, (a)(ii) a membrane directly contacts the ring of struts, and (a)(iii) the membrane is partially reticulated but not fully reticulated;
wherein the partially reticulated membrane includes: (b)(i) a void that forms a fluid path between the first and second cells, (b)(ii) an interface, between the partially reticulated membrane and the void, which is shredded;
wherein the SMP foam includes a composition, the composition including at least one of: (c)(i) N,N,N',N'-tetrakis (2-hydroxypropyl) ethylenediamine (HPED), triethanolamine (TEA), and hexamethylene diisocyanate (HDI) with TEA contributing a higher molar ratio of hydroxyl groups than HPED; (c)(ii) HPED, TEA, and trimethylhexamethylenediamine (TMHDI) with HPED contributing a higher molar ratio of hydroxyl groups than TEA, or (c)(iii) HPED, glycerol, pentanediol, and HDI.

17. The system of claim 16 wherein the interface is not chemically etched.

18. The system of claim 16 wherein the SMP foam includes cells, including the first and second cells, which are anisotropic in shape and have unequal major and minor axes.

19. The system of claim 18, wherein:
the ring of struts defines an outer perimeter of the membrane and the void defines an inner perimeter of the membrane;
an outer membrane area for the membrane is an area bounded by the outer perimeter defining an area of the membrane before reticulation;
a void area is an area bounded by the inner perimeter defining an area of the void;
and the void area is between 25% and 75% of the outer membrane area.

20. The system of claim 19, wherein:
the interface defines a protuberance of the membrane that protrudes away from the ring of struts and toward a central region of the void; and
the ring of struts forms a complete ring that is unbroken.

21. The system of claim 20, wherein the SMP foam comprises:
a first contiguous fluid path between at least 5 cells, formed along an axis generally parallel to a major axis of the foam; and a second contiguous fluid path between an additional at least 5 cells, formed along an additional axis generally parallel to the major axis;
wherein a third axis, generally parallel to a minor axis of the foam, intersects at least one of the at least 5 cells and at least one of the additional at least 5 cells.

* * * * *

UNITED STATES PATENT AND TRADEMARK OFFICE
CERTIFICATE OF CORRECTION

PATENT NO.         : 10,647,037 B2
APPLICATION NO.    : 15/232619
DATED              : May 12, 2020
INVENTOR(S)        : Jennifer N. Rodriguez, Duncan J. Maitland and Thomas S. Wilson It is certified that error appears in the above-identified patent and that said Letters Patent is hereby corrected as shown below:

In the Specification

Column 20:
Line 66, "trimethylhexamethylenediamine" should be --trimethyl hexamethylene diisocyanate--;

Column 24:
Line 59, "trimethylhexamethylenediamine" should be --trimethyl hexamethylene diisocyanate--;

Column 26:
Line 38, "trimethylhexamethylenediamine" should be --trimethyl hexamethylene diisocyanate--.

Signed and Sealed this
Twenty-second Day of November, 2022

Katherine Kelly Vidal
*Director of the United States Patent and Trademark Office*